(12) United States Patent
Devitt et al.

(10) Patent No.: US 12,298,236 B1
(45) Date of Patent: May 13, 2025

(54) SYSTEMS AND METHODS FOR MONITORING A GAS STERILIZATION ENVIRONMENT

(71) Applicant: KYMANOX CORPORATION, Morrisville, NC (US)

(72) Inventors: Shaun R. Devitt, Audubon, PA (US); Nicholas F. Bruno, Pottstown, PA (US); Arthur G. Marlin, Jr., Willow Grove, PA (US); Thomas M. Moyer, Ambler, PA (US)

(73) Assignee: Kymanox Corporation, Morrisville, NC (US)

( * ) Notice: Subject to any disclaimer, the term of this patent is extended or adjusted under 35 U.S.C. 154(b) by 0 days.

(21) Appl. No.: 18/947,846

(22) Filed: Nov. 14, 2024

(51) Int. Cl.
*G01N 21/3504* (2014.01)
*A61L 9/00* (2006.01)

(52) U.S. Cl.
CPC ............ *G01N 21/3504* (2013.01); *A61L 9/00* (2013.01); *A61L 2209/111* (2013.01)

(58) Field of Classification Search
CPC .............................. G01N 21/3504; A61L 9/00
See application file for complete search history.

(56) References Cited

U.S. PATENT DOCUMENTS

| | | |
|---|---|---|
| 5,468,961 A | 11/1995 | Gradon et al. |
| 5,565,634 A | 10/1996 | Graessle et al. |
| 5,788,925 A | 8/1998 | Pai et al. |
| 5,886,348 A | 3/1999 | Lessure et al. |
| 6,532,794 B2 | 3/2003 | Wang et al. |
| 6,875,399 B2 | 4/2005 | McVey |
| 6,917,885 B2 | 12/2005 | Centanni |
| 7,132,657 B2 | 11/2006 | Smith |
| 7,132,659 B2 | 11/2006 | Starta et al. |
| 7,157,045 B2 | 1/2007 | McVey |
| 7,166,843 B2 | 1/2007 | May |
| 7,626,168 B2 | 12/2009 | Fischer et al. |
| 7,687,776 B2 | 3/2010 | Baliga et al. |
| 7,835,004 B2 | 11/2010 | Uber et al. |
| 7,880,887 B2 | 2/2011 | Olson et al. |
| 8,955,340 B2 | 2/2015 | Burke et al. |
| 8,999,236 B2 | 4/2015 | Kanno et al. |
| 9,322,774 B2 | 4/2016 | Moenkemoeller |
| 9,678,010 B2 | 6/2017 | Starta et al. |
| 10,010,636 B2 | 7/2018 | Henniges |

(Continued)

FOREIGN PATENT DOCUMENTS

| | | |
|---|---|---|
| CN | 204854791 U | 12/2015 |
| CN | 211382879 U | 9/2020 |

(Continued)

*Primary Examiner* — David P Porta
*Assistant Examiner* — Meenakshi S Sahu
(74) *Attorney, Agent, or Firm* — Mills IP Law, PLLC

(57) ABSTRACT

Systems and methods are provided for monitoring a gas sterilization environment. The sensor assembly includes a housing that defines an internal chamber and a sensing volume that is in fluid communication with the gas sterilization environment. A gas concentration sensor and at least one environmental sensor positioned within the internal chamber and operably coupled to the sensing volume. A sensor-assembly controller is configured to execute a set of operations that control the sensors to monitor the gas sterilization environment over a sterilization period of between six hours and 48 hours.

20 Claims, 11 Drawing Sheets

(56) References Cited

U.S. PATENT DOCUMENTS

| | | |
|---|---|---|
| 10,022,464 B2 | 7/2018 | Sarphati et al. |
| 10,168,211 B1 | 1/2019 | Emadi et al. |
| 10,258,706 B2 | 4/2019 | Henniges et al. |
| 10,288,559 B2 | 5/2019 | Muniraju et al. |
| 10,338,021 B2 | 7/2019 | Graunke |
| 10,368,958 B2 | 8/2019 | Wherle et al. |
| 10,583,214 B2 | 3/2020 | Childers et al. |
| 10,780,191 B2 | 9/2020 | Stadler et al. |
| 10,948,445 B2 | 3/2021 | Raible et al. |
| 10,983,103 B2 | 4/2021 | Stokoe et al. |
| 11,156,577 B2 | 10/2021 | Graunke |
| 11,389,556 B2 | 7/2022 | Henniges et al. |
| 2002/0034823 A1 | 3/2002 | Kuepper et al. |
| 2003/0063997 A1 | 4/2003 | Fryer et al. |
| 2005/0260760 A1 | 11/2005 | Hucker |
| 2015/0374868 A1* | 12/2015 | Bruce .................... A61L 2/208 422/119 |
| 2017/0224859 A1 | 8/2017 | Broninx et al. |
| 2020/0179551 A1 | 6/2020 | Childers et al. |
| 2020/0390923 A1 | 12/2020 | Matta et al. |
| 2021/0181135 A1 | 6/2021 | Santoro, Jr. et al. |
| 2021/0199635 A1 | 7/2021 | Stokoe et al. |
| 2022/0008590 A1 | 1/2022 | Schweizer |
| 2022/0184262 A1 | 6/2022 | Xia et al. |
| 2022/0296741 A1 | 9/2022 | Henniges et al. |
| 2022/0296757 A1 | 9/2022 | Henniges et al. |
| 2022/0370671 A1 | 11/2022 | Starkweather et al. |
| 2022/0373568 A1 | 11/2022 | Scheffler et al. |
| 2023/0302176 A1 | 9/2023 | Bernard |

FOREIGN PATENT DOCUMENTS

| | | |
|---|---|---|
| CN | 115400248 A | 11/2022 |
| CN | 217724160 U | 11/2022 |
| DE | 202011050118 | 6/2011 |
| DE | 102015109415 | 12/2016 |
| EP | 1647284 | 4/2006 |
| EP | 3163295 | 5/2017 |
| GB | 2331810 | 6/1999 |
| WO | WO2001045754 | 6/2001 |
| WO | WO2010134826 | 11/2010 |
| WO | WO2019126533 | 6/2019 |
| WO | WO2023084337 | 5/2023 |

* cited by examiner

SYSTEMS AND METHODS FOR MONITORING A GAS STERILIZATION ENVIRONMENT

BACKGROUND

The embodiments described herein relate to systems and methods for method for monitoring a gas sterilization environment. In particular, this disclosure relates to a sensor assembly and methods of using the sensor assembly to determine a sterilant gas concentration of a designated sterilization period.

Certain industrial products, such as medical articles, must be sterilized before use. Some known sterilization processes include placing the product to be sterilized in a sterilization environment within a sterilization chamber. The sterilization process can, for example, expose the sterilization target to steam, irradiation, a sterilant gas, or combinations thereof over a specified interval to deactivate bacteria and/or viruses. The specific target values for the duration, environmental conditions within the sterilization chamber, the radiation dose, sterilant gas concentration, and/or combinations thereof depend on the sterility requirements for the sterilization target (i.e., the product).

Following the exposure of the sterilization target to sterilization, some known processes use microbiological testing (e.g., spore strips) to demonstrate sterility during a validation procedure and/or routine processing. However, microbiological methods have known challenges in reliability and a negative effect on processing timelines. For example, it is particularly challenging for microbiological testing to ensure sterility at or above desired levels of reliability, also referred to as the sterility assurance level (e.g., less than 106 product units being nonsterile). Additionally, there is often a lengthy delay (e.g., 24 hours or longer) in verifying sterility using microbiological testing. Such a delay can have an undesirable negative effect on processing timelines. Accordingly, with some known systems, the sterilization processes are controlled and monitored by directly measuring the process state variables (i.e., the system state conditions that inactivate microorganisms over a specified time) to ensure efficacy of the sterilization. With steam-based sterilization, for example, the process state variables can include temperature, pressure, and steam quality, while the process state variables for irradiation sterilization processes can be the absorbed dose. So long as the monitored process state variables are within specified ranges for specified durations, the sterility of the sterilization target is presumed.

In order to verify the sterility of the sterilization target via the monitoring of process state variables, it is desirable that the sensors monitoring the process state variables be placed in proximity to the sterilization target. For example, in some known systems, the sterilization target can include a number of industrial products or containers of products arranged in a stack or on a support rack. Collectively, the multiple industrial products or containers of products arranged in a stack or on a support rack is known as a "load." In such an implementation, it is desirable that the process state variables be monitored within the load rather than merely within the greater sterilization environment of the sterilization chamber. For example, with steam-based sterilization and/or irradiation sterilization processes, at least one sensor can be placed within the load to verify that the inner regions of the load (e.g., regions of the load surrounded by the industrial products or containers of products) have been exposed to process state variables that are within the specified ranges for the specified duration to ensure sterility.

In contrast to the steam-based and irradiation sterilization processes, processes that utilize a sterilant gas, such as ethylene oxide, do not currently have process state variable monitoring that effectively spatially covers the load including the inner regions of the load. Accordingly, validation and routine monitoring of gas sterilization processes often rely on microbiological testing to verify sterility. In some known gas sterilization systems, however, process variable monitoring is achieved but with at most a few sensors (often with a single sensor) located on the perimeter of the sterilization chamber. For example, in some known systems, the process state variables within the sterilization chamber are extrapolated from monitored process state variables within a duct through which the sterilant gas is introduced into the sterilization chamber. Due to the positioning of the sensors in such known systems, the results of the monitoring can, at best, correspond to the process state variables generally present within the sterilization chamber but do not reliably correlate to the process state variables in proximity to the load, much less within the inner regions of the load. Therefore, the use of sensors to monitor the process state variables of known gas sterilization systems gives little to no assurance of sterilization process conditions within the product load.

For the gas sterilization systems that use sensors to monitor the process state variables, the positioning of the sensors on the perimeter of or external to the sterilization chamber can be dictated by the power necessary to monitor the gas sterilization process over the duration of the process. For example, known gas sterilization processes can have a duration that exceeds 12 hours. In some instances, known gas sterilization processes can have a duration of 48 hours. Accordingly, access to sufficient power to support the continuous operation of the sensor over the sterilization process duration is desirable. Due to their high power requirements, some known sensors are tethered to an external power source. This arrangement, however, can be undesirable because it can result in a non-sealed sterilization chamber, can limit the ability to arrange the sensors in the desired spatial positions, and can result in potential hazards associated with transmitting power within a flammable environment (e.g., ethylene oxide).

Due at least in part to the limited awareness of the process state variables within the load, some known gas sterilization processes introduce sterilant gas into the gas chamber at concentrations and dwell times greater than would otherwise be required to satisfy the sterilization requirements. Such processes establish the sterilant gas concentration within the gas sterilization environment at a concentration that is deemed sufficient to establish a gas concentration within the load that at least satisfies a minimal concentration requirement. In other words, in an effort to ensure that a sufficient quantity of sterilant gas reaches the inner regions of the load, more sterilant gas than would otherwise be necessary is introduced into the gas chamber. However, some sterilant gases are hazardous at sufficient concentrations. For example, ethylene oxide has known short-term and long-term health consequences associated with exposure and is also explosive at sufficient concentrations. Due to the risks associated with certain sterilant gases it is desirable to minimize the amount of such sterilant gases while still ensuring sterilization within the load.

The use of more sterilant gas than would otherwise be necessary can also negatively impact the throughput of the gas sterilization process. For example, excess concentrations and dwell times permit the sterilant gas to be absorbed into product materials, especially polymers, to a greater degree than necessary for sterilization. Due to this absorption, an extend period of desorption is required after sterilization to render product safe for use. This extended period greatly reduces the throughput of the system.

Accordingly, there is a need for improved systems and methods for monitoring a sterilization environment.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter.

In some embodiments, the present disclosure is directed to a sensor assembly for monitoring a gas sterilization environment. The sensor assembly includes a housing, a gas concentration sensor, at least one environmental sensor, an energy storage device, and a sensor-assembly controller. The housing has a wall that at least partially defines an internal chamber and a sensing volume. The sensing volume is in fluid communication with the gas sterilization environment and fluidically isolated from the internal chamber. The gas concentration sensor is positioned within the internal chamber. The gas concentration sensor is operably coupled to the sensing volume. The at least one environmental sensor is positioned within the internal chamber. The at least one environmental sensor is operably coupled to the sensing volume. The energy storage device is positioned within the internal chamber and operably coupled to the gas concentration sensor and the at least one environmental sensor. The sensor-assembly controller includes a processor and a memory module. The sensor-assembly controller is operably coupled to the gas concentration sensor, the at least one environmental sensor, and the energy storage device. The sensor-assembly controller is configured to execute a set of operations to monitor the gas sterilization environment over a sterilization period of between six hours and 48 hours.

In some embodiments, the sensor assembly has a volume of between 150 milliliters and 450 milliliters defined by a set of maximal external dimensions of the sensor assembly.

In some embodiments, the sensor assembly is configured for use in any of a flammable environment or an explosive environment.

In some embodiments, the set of operations includes sampling via the gas concentration sensor and the at least one environmental sensor at a sampling rate of at least twice per minute and no more than 12 times per minute over the sterilization period. The sensor-assembly controller is configured to perform the set of operations while disconnected from any external power source and any external instrument.

In some embodiments, the sensor assembly is a stand-alone sensor assembly that is configured to operate devoid of any connection to an external instrument.

In some embodiments, the energy storage device has a capacity in a range of 2.0 ampere-hours to 3.5 ampere-hours.

In some embodiments, the sensor-assembly controller, the gas concentration sensor, and the at least one environmental sensor have a combined maximal power draw in a range of 75 milliamperes and 175 milliamperes.

In some embodiments, the sensor-assembly controller, the gas concentration sensor, and the at least one environmental sensor have a combined average power draw during the sterilization period in a range of 0.15 watts and 0.35 watts.

In some embodiments, the set of operations includes sampling via the gas concentration sensor and the at least one environmental sensor at a sampling rate of at least twice per minute and no more than 12 times per minute over the sterilization period. The sterilization period is a continuous interval.

In some embodiments, the housing includes an observation portion. The sensor-assembly controller is operably coupled to a status indicator positioned within the internal chamber. The status indicator is visible through the observation portion and is configured to produce an indication of an operating status of the sensor assembly.

In some embodiments, the sensor assembly includes an end cap and a seal member removably coupled to the housing, the end cap and the seal member hermetically sealing the internal chamber on a condition that the end cap and seal member are coupled to the housing.

In some embodiments, the sensor-assembly controller includes a data port positioned within the internal chamber. The data port is isolated from the gas sterilization environment on a condition that the internal chamber is hermetically sealed. The data port is accessible on a condition that the end cap is decoupled from the housing.

In some embodiments, the sensor assembly includes a breach indicator positioned within the internal chamber, the breach indicator is configured to generate a signal on a condition of a failure of a hermetic seal of the internal chamber.

In some embodiments, the housing includes an observation portion. The breach indicator is a chemical indicator that is visible through the observation portion. The chemical indicator has a first color and a second color. The second color is indicative of an exposure of the chemical indicator to a portion of a sterilant gas.

In some embodiments, the housing has an absence of a defined sensing orientation on a condition that the sensor assembly is positioned within the gas sterilization environment.

In some embodiments, the housing is at least partially surrounded by a gas-permeable filter. The gas-permeable filter is positioned so that the fluid communication between the sensing volume and the gas sterilization environment is via the gas-permeable filter.

In some embodiments, the gas sterilization environment includes an invisible sterilant gas. The gas concentration sensor is a non-dispersive infrared gas concentration sensor with an emitter portion and a detector portion. The emitter portion and the detector portion are operably coupled to the sensing volume. The non-dispersive infrared gas concentration sensor is configured to output a signal corresponding to a concentration of the invisible sterilant gas within the sensing volume.

In some embodiments, the non-dispersive infrared gas concentration sensor is a four-channel sensor.

In some embodiments, the non-dispersive infrared gas concentration sensor includes an emitter window positioned between the emitter portion and the sensing volume. The emitter window has a low heat capacity and is absorptive of blackbody radiation.

In some embodiments, the blackbody radiation is generated by the emitter portion of the non-dispersive infrared gas concentration sensor.

In some embodiments, the non-dispersive infrared gas concentration sensor includes a window heater operably coupled to the emitter window. The window heater is selectively actuated by the sensor-assembly controller. The set of operations includes actuating the window heater at a heating rate of between once per minute and 12 times per minute over the sterilization period.

In some embodiments, the non-dispersive infrared gas concentration sensor includes a receiver window positioned between the detector portion and the emitter portion. The receiver window has a low heat capacity and is absorptive of blackbody radiation.

In some embodiments, the non-dispersive infrared gas concentration sensor includes a window heater operably coupled to the receiver window. The window heater is selectively actuated by the sensor-assembly controller. The set of operations includes actuating the window heater at a heating rate of at least twice per minute and no more than 12 times per minute over the sterilization period.

In some embodiments, the at least one environmental sensor is at least one of a pressure sensor, a temperature sensor, or a humidity sensor.

In some embodiments, the at least one environmental sensor is self-heating. The self-heating mitigates an effect of condensation on the at least one environmental sensor following an exposure to a sterilant gas.

In some embodiments, the at least one environmental sensor is a pressure sensor. The sensor assembly further includes an integrated sensor package comprising a humidity sensor and a temperature sensor.

In some embodiments, the sensor assembly includes a wireless transmitter having an output signal that is configured to be received by an antenna element within a sterilization chamber during the sterilization period.

In some embodiments, the sensor assembly includes a positioning device configured secure the sensor assembly to one of a wall of a sterilization chamber, a support structure within the sterilization chamber, or a product support on a condition that the sensor assembly is positioned within the sterilization chamber.

In some embodiments, the positioning device is one of an actuatable magnet, a vacuum grip, a mechanical grip, an adhesive, a keyed protrusion, or a lanyard.

In some embodiments, the set of operations executed by the sensor-assembly controller manage a peak power consumption and an average power consumption of at least the gas concentration sensor and the at least one environmental sensor based on a capacity of the energy storage device to monitor the gas sterilization environment over the sterilization period of between six hours and 48 hours.

In some embodiments, the set of operations includes initiating a set of sampling intervals at a sampling rate for the gas concentration sensor and the at least one environmental sensor. Each sampling interval of the set of sampling intervals corresponds to a sampling of the gas sterilization environment via the gas concentration sensor and the at least one environmental sensor. The sampling rate corresponds to a period between an initiation of subsequent sampling intervals. The sampling rate is in a range of 5 seconds to 30 seconds during the sterilization period.

In some embodiments, each sampling interval includes an initiation phase and a measurement phase following the initiation phase. The initiation phase includes an initiation power consumption that is in a range 120 percent to 140 percent of a design power consumption magnitude. The measurement phase includes a measurement power consumption that is in a range of 80 percent to 100 percent of the design power consumption magnitude during a sampling of the gas sterilization environment. The set of operations includes initiating a standby phase following the measurement phase and preceding a subsequent initiation phase. The standby phase includes a standby power consumption in a range of 0 percent to 5 percent of the design power consumption magnitude.

In some embodiments, the measurement phase has a duration that is greater than a duration of the initiation phase. The standby phase has a duration that is greater than a combination of both the measurement phase duration and the initiation phase duration.

In some embodiments, the set of operations includes activating at least one window heater operably coupled to a window positioned between the gas concentration sensor and the sensing volume on a condition that the gas concentration sensor is in the standby phase.

In some embodiments, the set of operations includes determining, via the at least one environmental sensor, an ambient temperature of the gas sterilization environment. The set of operations also includes activating at least one window heater operably coupled to a window positioned between the gas concentration sensor and the sensing volume on a condition that the ambient temperature is below a minimum temperature threshold.

In some embodiments, the set of operations includes determining, via the at least one environmental sensor, a humidity level of the gas sterilization environment. The set of operations also includes activating at least one window heater operably coupled to a window positioned between the gas concentration sensor and the sensing volume on a condition that the humidity level exceeds a humidity threshold.

In some embodiments, the set of operations includes determining, via the at least one environmental sensor, an ambient temperature of the gas sterilization environment at each sampling interval. The set of operations also includes receiving an output from the gas concentration sensor indicative of a sensed sterilant gas concentration at each sampling interval. Additionally, the set of operations includes determining a correction factor at each sampling interval for the output from the gas concentration sensor based on the ambient temperature of the gas sterilization environment at the same sampling interval and applying the correction factor to the output from the gas concentration sensor at each sampling interval to determine a recorded sterilant gas concentration at each sampling interval.

In some embodiments, the sensing volume includes a first portion, a second portion, and a communication passage that fluidically couples the first portion of the sensing volume and the second portion of the sensing volume to the gas sterilization environment. A longitudinal axis of the first portion of the sensing volume is parallel to a longitudinal axis of the second portion of the sensing volume and is parallel to a longitudinal axis of the housing. The first portion of the sensing volume and the second portion of the sensing volume are each positioned at a distance from an axial midline of the housing with the axial midline is between the first portion of the sensing volume and the second portion of the sensing volume. The gas concentration sensor is operably coupled to the first portion of the sensing volume. The at least one environmental sensor is operably coupled to the second portion of the sensing volume.

In some embodiments, the present disclosure is directed to a method for monitoring a gas sterilization environment. The method includes actuating a sensor assembly. The sensor assembly includes a gas concentration sensor, at least one environmental sensor, an energy storage device, and a sensor-assembly controller configured to record a set of signals from the gas concentration sensor and the at least one environmental sensor associated with the sterilization environment at each sampling interval of a set of sampling intervals over a sterilization period of between six hours and 48 hours. The sensor assembly is devoid of any external data connections and power connections within the sterilization environment. The method also includes managing, via the sensor-assembly controller, a peak power consumption and an average power consumption of at least the gas concentration sensor and the at least one environmental sensor based on a capacity of the energy storage device to monitor the gas sterilization environment over the sterilization period of between six hours and 48 hours.

In some embodiments, actuating the sensor assembly includes actuating the gas concentration sensor and the at least one environmental sensor at a sampling rate of at least twice per minute and no more than 12 times per minute over the sterilization period.

In some embodiments, actuating the sensor assembly includes actuating the gas concentration sensor and the at least one environmental sensor at a sampling rate of at least four times per minute and less than nine times per minute over the sterilization period.

In some embodiments, the method includes transitioning the gas concentration sensor and the at least one environmental sensor to an inactive state at a conclusion of each sampling interval of the set of sampling intervals.

In some embodiments, each sampling interval of the set of sampling intervals includes an initiation phase followed by a measurement phase. The initiation phase has a duration that is in a range of 2% to 15% of a duration of each sampling interval of the set of sampling intervals. Managing the peak power consumption includes establishing at least the gas concentration sensor at an initiation power consumption during the initiation phase. Managing the average power consumption includes transitioning at least the gas concentration sensor toward a measurement power consumption concurrent with a transition from the initiation phase to the measurement phase. The initiation power consumption has a magnitude that is configured to minimize a time to a steady-state signal of at least the gas concentration sensor following an initiation of each sampling interval of the set of sampling intervals. The magnitude of the initiation power consumption is in a range of at least 1.2 to no more than 1.4 times a magnitude of the measurement power consumption. The measurement power consumption is in a range of at least 0.8 to no more than 1.0 times a design power consumption magnitude of the sensor assembly.

In some embodiments, the method includes activating at least one window heater operably coupled to a window positioned between the gas concentration sensor and a sensing volume.

In some embodiments, activating the at least one window heater includes activating the at least one window heater on a condition in which at least one of a humidity level exceeds a humidity threshold or an ambient temperature is below a minimum temperature threshold and maintaining the at least one window heater in an inactive state on a condition in which both the humidity level is below the humidity threshold and the ambient temperature is above the minimum temperature threshold.

In some embodiments, activating the at least one window heater includes activating the at least one window heater on a condition that each of the gas concentration sensor and the at least one environmental sensor are in an inactive state and maintaining the at least one window heater in an inactive state during each sampling interval of the set of sampling intervals.

In some embodiments, activating the at least one window heater includes activating the at least one window heater in accordance with a first heater duty cycle on a condition that an ambient temperature is within a first temperature range. Activating the at least one window heater includes activating the at least one window heater in accordance with a second heater duty cycle on a condition that the ambient temperature is within a second temperature range. The second heater duty cycle has a duration between sequential heater actuations that is greater than a duration between sequential heater actuations of the first heater duty cycle.

In some embodiments, the gas concentration sensor includes at least one window positioned between a portion of the gas concentration sensor and a sensing volume. The at least one window is absorptive of blackbody radiation emitted by the gas concentration sensor. Actuating the sensor assembly includes actuating the gas concentration sensor at a sampling rate configured to maintain the at least one window at a temperature within a specified temperature range.

In some embodiments, the gas concentration sensor is at least a 2-channel sensor. The set of signals includes signals associated with a measurement channel and a reference channel of the gas concentration sensor.

In some embodiments, the measurement channel has a target wavelength associated with an absorbance of ethylene oxide, and the reference channel has a target wavelength associated with an absorbance of neither a sterilant gas nor an environmental gas.

In some embodiments, the present disclosure is directed to a sensor assembly for monitoring a gas sterilization environment. The sensor assembly includes a housing, a gas concentration sensor, at least one environmental sensor, an energy storage device, and a sensor assembly. The housing has a wall that at least partially defines an internal chamber and a sensing volume. The sensing volume is in fluid communication with the gas sterilization environment and fluidically isolated from the internal chamber. The gas concentration sensor is positioned within the internal chamber. The gas concentration sensor is operably coupled to the sensing volume. The at least one environmental sensor is positioned within the internal chamber. The at least one environmental sensor is operably coupled to the sensing volume. The energy storage device is positioned within the internal chamber and operably coupled to the gas concentration sensor and the at least one environmental sensor. The sensor-assembly controller includes a processor and a memory module. The sensor-assembly controller is operably coupled to the gas concentration sensor, the at least one environmental sensor, and the energy storage device. The sensor-assembly controller is configured to execute a set of operations to monitor the gas sterilization environment over a sterilization period. The sensor-assembly controller is configured to perform the set of operations while disconnected from any external power source and any external instrument.

In some embodiments, the present disclosure is directed to a sensor assembly for monitoring a gas sterilization environment that is any of a flammable environment or an explosive environment. The sensor assembly includes a housing, a cover, a gas concentration sensor, at least one environmental sensor, an energy storage device, and a sensor assembly. The housing has a wall that at least partially defines an internal chamber and a sensing volume. The sensing volume is in fluid communication with the gas sterilization environment and fluidically isolated from the internal chamber. The cover is removably coupled to the housing. The internal chamber is exposed on a condition that the cover is removed from the housing. The cover and a seal member hermetically seal the internal chamber on a condition that the cover and seal member are coupled to the housing. The gas concentration sensor is positioned within the internal chamber. The gas concentration sensor is operably coupled to the sensing volume. The at least one environmental sensor is positioned within the internal chamber. The at least one environmental sensor is operably coupled to the sensing volume. The energy storage device is positioned within the internal chamber and operably coupled to the gas concentration sensor and the at least one environmental sensor. The sensor-assembly controller includes a processor and a memory module. The sensor-assembly controller is operably coupled to the gas concentration sensor, the at least one environmental sensor, and the energy storage device. The sensor-assembly controller is configured to execute a set of operations to monitor the gas sterilization environment over a sterilization period.

In some embodiments, the sensor-assembly controller is configured to perform the set of operations while disconnected from any external power source and any external instrument.

In some embodiments, the sensor assembly includes a breach indicator positioned within the internal chamber. The breach indicator is configured to generate a signal on a condition of a failure of a hermetic seal of the internal chamber.

DETAILED DESCRIPTION

Figure 1:
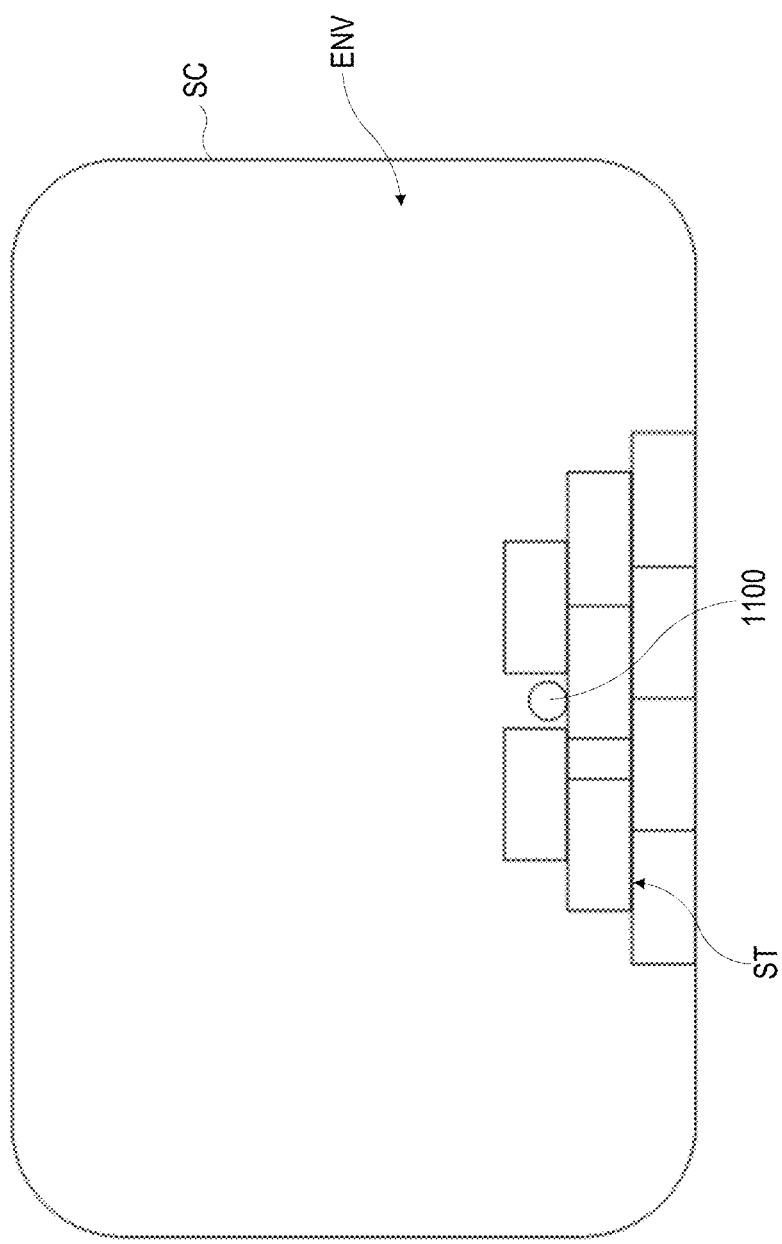
FIG. 1 is a schematic view of a sensor assembly positioned in a gas sterilization environment in a sterilization chamber according to an embodiment.

Generally, the present disclosure is directed to systems and methods for monitoring a gas sterilization environment within a sterilization chamber to ensure the sterility of a sterilization target (e.g., a "load" that includes multiple products or containers of products arranged in a stack or on a support rack). The gas sterilization environment can, for example, use a sterilant gas (e.g., ethylene oxide) that is not visible to the naked eye. As described herein, the process state variables of the gas sterilization environment are monitored via at least one sensor assembly. The process state variables include the concentration of the sterilant gas and at least one environmental parameter, such as humidity, temperature, and/or pressure. Each of the process state variables can be monitored at each of a series of sampling intervals over a sterilization period to ensure that the sterilization target has been exposed to process state variables that are within specified ranges for the specified duration to ensure sterility. The sterilization period can, for example, extend from the sealing of the sterilization chamber at the initiation of the sterilization process to the removal of the load from the sterilization chamber at the conclusion of the sterilization process. This period can, in some instances, be at least six hours and no more than 48 hours in duration.

The sensor assemblies described herein are sized to be positioned within the load. In other words, the sensor assemblies are of a suitable size to be positioned in and amongst multiple products or containers of products of the load in order to monitor the process state variables in the inner regions of the load. Thus positioned, the sensor assemblies can be used to monitor the process variables closely surrounding and throughout the load, including regions that cannot be accurately monitored via a sensor positioned externally to the load (e.g., along the perimeter of the sterilization chamber). Insofar as the process state variables can be monitored in the inner regions of the load, the sterility of the entire load can be confirmed based on the process state variables within the load being within the specified ranges for the specified duration to ensure sterility. This, in turn, reduces or eliminates the requirement to introduce sterilant gas into the gas chamber at concentrations greater than would otherwise be required to satisfy the sterilization requirements in order to presumptively establish a gas concentration within the load that at least satisfies a minimal concentration requirement.

In that some sterilant gases, such as ethylene oxide, are hazardous at sufficient concentrations, the reduction or elimination of the requirement to introduce excess sterilant gas is desirable due to the corresponding reduction in the risks associated with the use of the sterilant gas. For example, the use of the sensor assemblies described herein can facilitate the use of a lesser quantity of ethylene oxide by confirming that the actual concentration of ethylene oxide within the load is sufficient to satisfy the sterilization parameters even at lower concentrations of the sterilant gas within the sterilization chamber. In other words, by recording the actual process state variables within the load, the actual process state variables can be correlated to lower concentrations of sterilant gas introduced into the sterilization chamber. Subsequently, the concentration of sterilant gas introduced into the sterilization chamber can be set at a magnitude that establishes the actual process state variables within the load at a level sufficient to satisfy the sterilization parameters, and the sterility of the product can be verified via the recorded process state variables from the sensor assemblies. In the case of gas sterilization processes that use ethylene oxide, the reduction in the amount of ethylene oxide required to establish the process state variables at a level that satisfies the sterilization parameters mitigates the hazards associated with the use of ethylene oxide. Additionally, the reduction in the amount of ethylene oxide required to establish the process state variables at a level that satisfies the sterilization parameters can increase the throughput of the gas sterilization system by reducing or eliminating the extended period of desorption and related post treatment processing (e.g., aeration, air washing, and/or air rinsing) that would otherwise be required at higher concentrations of sterilant gas.

One of the hazards associated with the use of certain sterilant gases, such as ethylene oxide, is the flammability or even explosiveness of the sterilant gas at sufficient concentrations. Accordingly, the sensor assemblies described herein are constructed to maximize their intrinsic safety. Intrinsic safety refers to a condition in which the available energy is at a level that is too low to cause ignition of the flammable/explosive gas. For example, the housing of the sensor assembly can be formed from a material and have a shape that are selected to minimize or eliminate a sparking potential between the sensor assembly and a contacted object. Said another way, the material and/or the shape of the housing assembly can be selected so that in the event the sensor assembly is dislodged and falls to the floor of the sterilization chamber, no spark will result from the impact. Additionally, the intrinsic safety of the sensor assemblies is furthered by configuring the electronic components to prevent sparking conditions and have peak temperatures that are below a threshold that may otherwise cause an explosive hazard. Said another way, the electronics of the sensor assemblies, including an energy storage device, have an energy level that is below an ignition threshold of the sterilant gas (e.g., the ignition threshold of ethylene oxide at the concentrations within the sterilization environment). The intrinsic safety of the sensor assemblies is also furthered by configuring the electronic components within a hermetically sealed within an internal chamber that is isolated from the sensing volume, thereby limiting the likelihood that the flammable gas will be in proximity to certain electronic components.

In some embodiments as described herein, the sensor assembly for monitoring the gas sterilization environment can include a housing, a gas concentration sensor, at least one environmental sensor, an energy storage device, and a sensor-assembly controller. The sensor assembly is portable and is sized to be positioned within the load within the sterilization chamber without electronic tethers. For example, the sensor assembly is not tethered to an external power source nor any external sensors. Said another way, the sensor assembly can be a self-contained sensor assembly without any electronic couplings during the sterilization. As the sensor assembly is not coupled to an external power source, the energy storage device must contain sufficient energy to support the operations of the sensor assembly (e.g., the sensors, the sensor-assembly controller, and any additional power-consuming components of the sensor assembly) over a sterilization period of at least six hours and up to 48 hours. However, the dimensions of the sensor assembly (i.e., the housing) establish a maximum physical size of the energy storage device, while the requirement for intrinsic safety further limits the operating parameters of the energy storage device. Accordingly, the sensor-assembly controller is configured to operate the sensor assembly within a limited power budget based on the capacity of the energy storage device as constrained by the physical dimensions of the sensor assembly and the requirement for intrinsic safety in the absence of an external power source. More specifically, the sensor-assembly controller manages the power consumption of the sensor assembly to ensure the continued operation of the sensor assembly throughout the duration of the sterilization period.

As used herein, the term "about" when used in connection with a referenced numeric indication means the referenced numeric indication plus or minus up to 10 percent of that referenced numeric indication. For example, the language "about 50" covers the range of 45 to 55. Similarly, the language "about 5" covers the range of 4.5 to 5.5.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

The term "visible" when used in connection with a gas being detected by any of the systems and methods described herein refers to gases with peak absorbance light wavelength in the visible spectrum (400 to 760 nanometers) or otherwise having significant absorbance (an absorption coefficient of >1 $cm^{-1}$) in the visible spectrum. Nonvisible gases (also referred to as invisible gases) include any gases that are not visible. One nonlimiting example of an invisible gas is ethylene oxide.

FIG. 1 is a schematic view of a sensor assembly 1100 positioned in a sterilization environment ENV in a sterilization chamber SC according to an embodiment. The sterilization chamber SC is an enclosed space configured to receive at least one sterilization target ST, to be sealed relative to an external environment, and to establish the sterilization environment ENV therein. In some embodiments, the sterilization environment ENV is a gas sterilization environment. Accordingly, the sterilization environment ENV is an environment that includes environmental parameters and at least one sterilant gas (e.g., ethylene oxide, gaseous hydrogen peroxide, ozone, formaldehyde, nitrogen dioxide, and/or gaseous mixtures) configured to deactivate microorganisms (e.g., viruses and/or bacteria) such that the sterilization target ST is sterilized. Similarly stated, the sterilization environment ENV is produced and maintained for a time period sufficient to meet the sterility assurance level (SAL; e.g., the probability of a microorganism surviving on the sterilization target ST being less than one in a million). In some embodiments, the sterilization environment ENV is a flammable and/or explosive environment based on the presence of a sufficient concentration of the sterilant gas. Accordingly, in some embodiments the sensor assembly 1100 is configured for use in such a flammable and/or explosive environment.

As depicted in FIG. 1, the sensor assembly 1100 is sized to be at least partially surrounded by sterilization targets ST. The totality of the sterilization targets ST positioned within the sterilization chamber SC can be collectively referred to as the "load" and can include a stack or other arrangement of multiple sterilization targets and/or containers of sterilization targets. Accordingly, the sensor assembly 1100 can be sized to be positioned within the load (e.g., within a stack of sterilization targets ST) within the sterilization chamber SC. The sensor assembly 1100 can be separated from the walls of the sterilization chamber SC and can have an absence of an electrical coupling to any external power source (e.g., line power, an external battery, and/or a power supply of the sterilization chamber SC). Said another way, in some embodiments, the sensor assembly 1100 (and any of the sensor assemblies described herein) can be stand-alone devices that include all necessary components, power supplies, substances, and subassemblies to perform any of the gas sensing methods described herein. Such stand-alone devices do not require any external instrument to manipulate or otherwise process the gas samples to be measured, and do not require any connection to an external power source to complete the methods described herein. Thus, the sensor assemblies described herein can be fully-contained and upon being placed into the sterilization environment ENV, the sensor assembly can be actuated to perform the environmental monitoring described herein.

Figure 2:
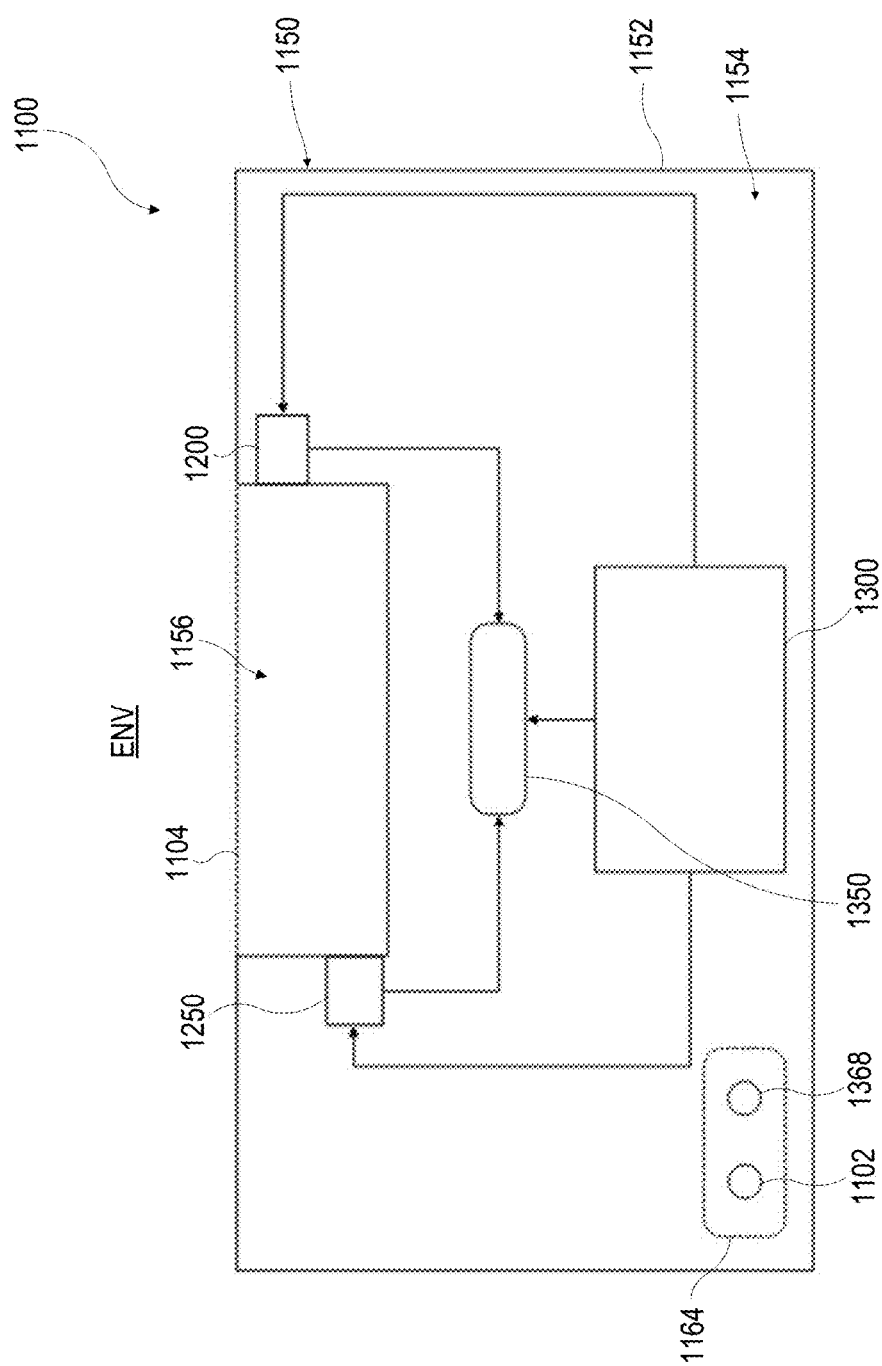
FIG. 2 is a schematic view of the sensor assembly of FIG. 1 according to an embodiment.

FIG. 2 is a schematic view of the sensor assembly 1100 for monitoring the sterilization environment ENV in the sterilization chamber SC. The sensor assembly 1100 includes a housing 1150, a gas concentration sensor 1200, at least one environmental sensor 1250, an energy storage device 1300, and a sensor-assembly controller 1350. To facilitate placement of the sensor assembly 1100 within and around the load, a set of maximal external dimensions of the housing 1150 can define a volume of the sensor assembly 1100 of between 150 mL and 450 mL. Said another way, the housing 1150 can be sized to be supported in a single hand of an operator.

The housing 1150 includes a wall 1152 that can, in some embodiments, be formed from a noncombustible and/or non-sparking material. For example, housing can be formed from aluminum or stainless steel. The wall 1152 defines an internal chamber 1154 and a sensing volume 1156. The sensing volume 1156 is in fluid communication with the sterilization environment ENV. In some embodiments, the fluid communication between the sensing volume 1156 and the sterilization environment ENV is via a gas-permeable filter 1104 that at least partially surrounds the housing 1150. The sensing volume 1156 is fluidically isolated from the internal chamber 1154. Additionally, the internal chamber 1154 can be fluidically isolated from the sterilization environment ENV. In some embodiments, the internal chamber 1154 can be hermetically sealed. Said another way, the internal chamber 1154 can be configured to be fully sealed such that an interaction between any electronics and/or polymer materials placed therein and the sterilization environment ENV is eliminated or minimized. This arrangement facilitates using the sensor assembly 1100 in such a flammable and/or explosive environment.

In some embodiments, the gas concentration sensor 1200 is positioned within the internal chamber 1154 and is operably coupled to the sensing volume 1156. Being operably coupled to the sensing volume 1156, which is in fluid communication with the sterilization environment ENV, the gas concentration sensor 1200 is positioned to monitor a concentration of the sterilant gas within the sterilization environment ENV. For example, in some embodiments, the sterilization environment ENV includes an invisible sterilant gas, such as ethylene oxide, and the gas concentration sensor 1200 can be a non-dispersive infrared gas concentration sensor. The non-dispersive infrared gas concentration sensor can transmit and receive infrared radiation through the sensing volume 1156 via a window (e.g., a sapphire window, not shown in FIG. 2) in order to determine the concentration of the invisible sterilant gas based on a detected decrease in transmitted infrared radiation within the sensing volume 1156.

In some embodiments, each environmental sensor 1250 is positioned within the internal chamber 1154. Each environmental sensor 1250 is also operably coupled to the sensing volume 1156. The operable coupling of each environmental sensor 1250 to the sensing volume 1156 can be via a sensor membrane or other sensor surface that is nonreactive with the sterilant gas. The environmental sensor 1250 can, for example, be a pressure sensor, a temperature sensor, and/or a humidity sensor. Accordingly, each environmental sensor 1250 can be used to measure an ambient temperature, a humidity, and/or a pressure level of the sterilization environment ENV.

As depicted in FIG. 2, the energy storage device 1300 is positioned within the internal chamber 1154. The energy storage device 1300 is operably coupled to the gas concentration sensor 1200, each environmental sensor 1250, the sensor-assembly controller 1350, and any additional electronic components of the sensor assembly 1100. In some embodiments, the energy storage device 1300 can be a battery that has previously passed intrinsic safety testing or is included in an intrinsic safety test of the sensor assembly 1100. The energy storage device 1300 can be rechargeable or replaceable on a condition that the sensor assembly 1100 is positioned outside of the sterilization chamber SC. For example, a charging port can be positioned within the internal chamber 1154 and accessed by opening (e.g., unsealing) a portion of the housing 1150, such as an end cap (not shown). In other embodiments, the energy storage device 1300 (or any of the energy storage devices described herein) can be any other suitable energy storage device, such as capacitors or magnetic energy storage devices.

The energy storage device 1300 (e.g., the battery) can have a sufficient capacity to maintain operations of the powered components of the sensor assembly 1100 during the entirety of the sterilization period. In some embodiments, the energy storage device 1300 can have a capacity in a range of 2.0 ampere-hours to 3.5 ampere-hours. For example, the battery can be a 3.0 ampere-hour battery with 8.7 watt-hours of total energy. In view of the absence of an external power source and capacity of the energy storage device 1300, in some embodiments, the sensor-assembly controller 1350, the gas concentration sensor 1200, each environmental sensor 1250, and any additional powered components of the sensor assembly 1100 have a combined maximal power draw in a range of between 50 mA and 275 mA (e.g., between 75 mA and 175 mA) and a combined average power draw during the sterilization period in a range of 0.15 watts and 0.35 watts. For example, the sensor-assembly controller 1350, the gas concentration sensor 1200, each environmental sensor 1250, and any additional powered components of the sensor assembly 1100 have a combined maximal current draw in a range of between 50 mA per hour and 275 mA per hour (e.g., between 75 mA per hour and 175 mA per hour).

In some embodiments, the sensor-assembly controller 1350 can include a processor (not shown) and a memory module (not shown). As depicted, the sensor-assembly controller 1350 is operably coupled to at least the gas concentration sensor 1200, each environmental sensor 1250, and the energy storage device 1300. As described in more detail below, the sensor-assembly controller 1350 is configured to execute a set of operations to monitor the sterilization environment ENV over a sterilization period of at least six hours and no more than 48 hours. In other embodiments, the sterilization period can be between about six hours and 36 hours. In yet other embodiments, the sterilization period can be between about six hours and 24 hours.

As further depicted in FIG. 2, in some embodiments, the sensor assembly 1100 includes a status indicator 1368 that is operably coupled to the sensor-assembly controller 1350. The status indicator 1368 is configured to produce an indication of an operating status of the sensor assembly 1100. In some embodiments, a status indicator 1368 is positioned within the internal chamber 1154 and is visible through an observation portion 1164 of the housing 1150. The observation portion 1164 can be a visually transparent portion of the wall 1152.

In some embodiments, the sensor assembly 1100 includes a breach indicator 1102. The breach indicator 1102 is positioned within the internal chamber 1154. The breach indicator 1102 is configured to generate a signal should the hermetic seal of the internal chamber 1154 fail, resulting in the internal chamber 1154 (and the components contained therein) being exposed to the sterilant gas. In some embodiments, the signal can be a visual signal. In such embodiments, breach indicator 1102 can be visible via the observation portion 1164 of the housing 1150. The breach indicator 1102 can, for example, be a chemical indicator characterized by a first color and a second color. The first color can be indicative of an absence of exposure to the sterilant gas, while the second color can be indicative of an exposure to the sterilant gas. Thus, the breach indicator 1102 can produce the second color on the condition that the internal chamber has been exposed to sterilant gas. The chemical indicator can be nonreactive to environmental conditions outside of the sterilization chamber SC. Accordingly, the internal chamber 1154 can be disrupted (e.g., open) on a condition that the sensor assembly 1100 is positioned outside of the sterilization chamber SC without causing the chemical indicator to transition from the first color to the second color.

FIGS. 3-9 depict various aspects of a sensor assembly 2100 for monitoring a sterilization environment ENV within a sterilization chamber (not shown) according to an embodiment. In some embodiments, the sterilization environment ENV is a gas sterilization environment. Accordingly, the sterilization environment ENV is an environment that includes environmental parameters and at least one sterilant gas (e.g., ethylene oxide, gaseous hydrogen peroxide, ozone, formaldehyde, nitrogen dioxide, and/or gaseous mixtures) configured to deactivate microorganisms (e.g., viruses and/or bacteria) such that the sterilization target is sterilized. In some embodiments, the sterilization environment ENV is a flammable and/or explosive environment based on the presence of a sufficient concentration of the sterilant gas. Accordingly, in some embodiments the sensor assembly 2100 is configured for use in such a flammable and/or explosive environment.

The sensor assembly 2100 is sized to be at least partially surrounded by sterilization targets. The totality of the sterilization targets positioned within the sterilization chamber can be collectively referred to as the "load" and can include a stack or other arrangement of multiple sterilization targets and/or containers of sterilization targets as depicted in FIG. 1. Accordingly, the sensor assembly 2100 can be sized to be positioned within the load (e.g., within a stack of sterilization targets) within the sterilization chamber. The sensor assembly 2100 can be separated from the walls of the sterilization chamber and can have an absence of an electrical coupling to any external power source (e.g., line power, an external battery, and/or a power supply of the sterilization chamber). Said another way, in some embodiments, the sensor assembly 2100 (and any of the sensor assemblies described herein) can be stand-alone devices that include all necessary components, power supplies, substances, and subassemblies to perform any of the gas sensing methods described herein. Such stand-alone devices do not require any external instrument to manipulate or otherwise process the gas samples to be measured, and do not require any connection to an external power source to complete the methods described herein. Thus, the sensor assemblies described herein can be fully-contained and upon being placed into the sterilization environment ENV, the sensor assembly can be actuated to perform the environmental monitoring described herein.

In some embodiments, the sensor assembly 2100 includes a housing 2150, a gas concentration sensor 2200, at least one environmental sensor 2250, an energy storage device 2300, and a sensor-assembly controller 2350. To facilitate placement of the sensor assembly 2100 within and around the load, a set of maximal external dimensions (e.g., a maximal length L and a maximal diameter D) of the housing 2150 can define a volume of the sensor assembly 2100 of between 150 mL and 450 mL. Said another way, the housing 1150 can be sized to be supported in a single hand of an operator.

Figure 3:
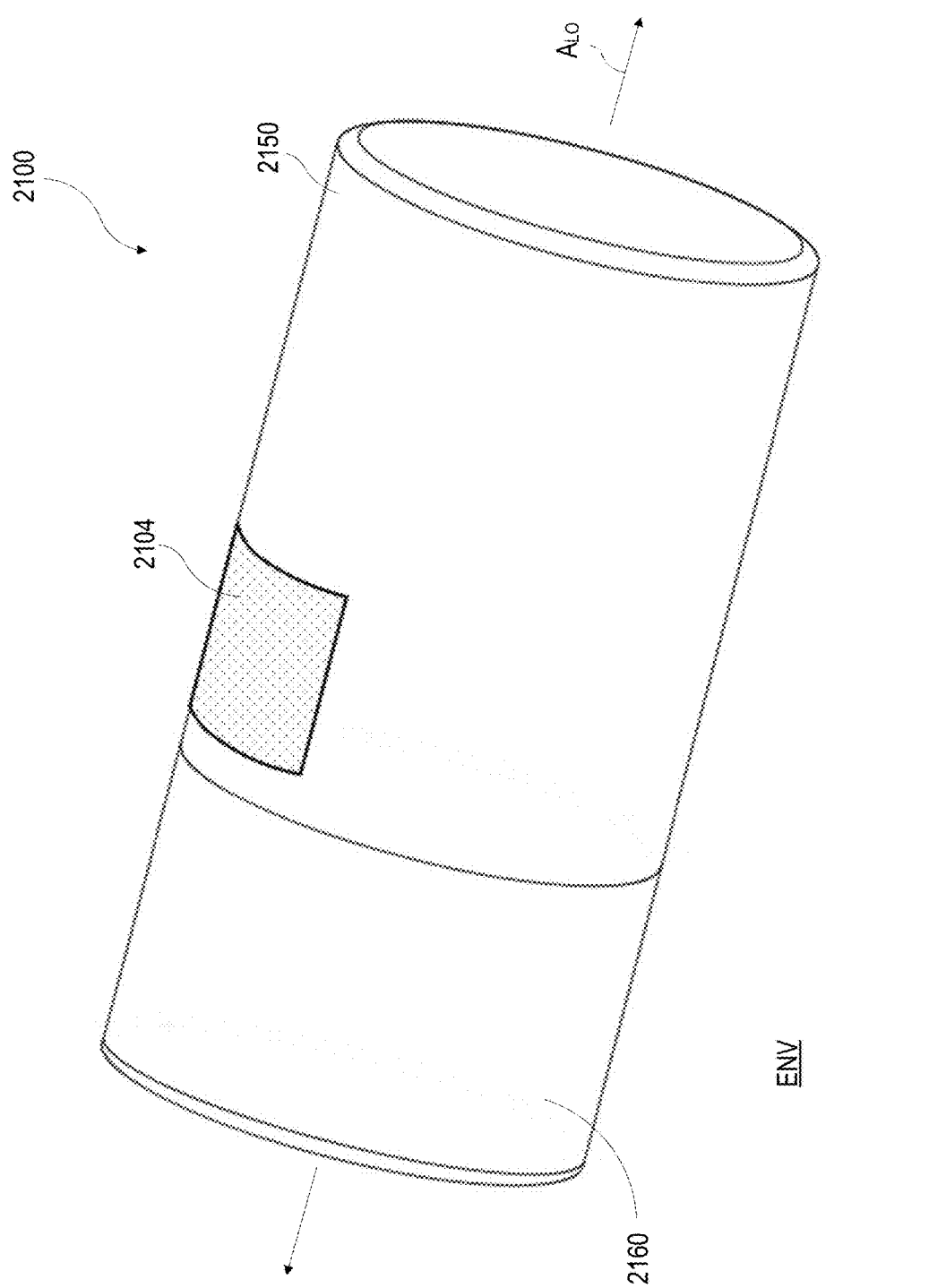
FIG. 3 is a perspective view of a sensor assembly for monitoring a gas sterilization environment according to an embodiment.

As depicted in FIG. 3, in some embodiments, the sensor assembly 2100 (i.e., the housing 2150) has a cylindrical shape. However, in additional embodiments, the sensor assembly 2100 can have an ellipsoid shape, a spherical shape, a rectilinear shape, or combinations and modifications thereof. Additionally, in some embodiments, the sensor assembly 2100 (i.e., the housing 2150) has an absence of a defined sensing orientation on a condition that the sensor assembly 2100 is positioned within the sterilization environment ENV. Said another way, in some embodiments, the sensor assembly 2100 and/or the housing 2150 can effectively and accurately monitor the sterilization environment irrespective of the orientation at which the sensor assembly is placed within the sterilization environment ENV.

Figure 5:
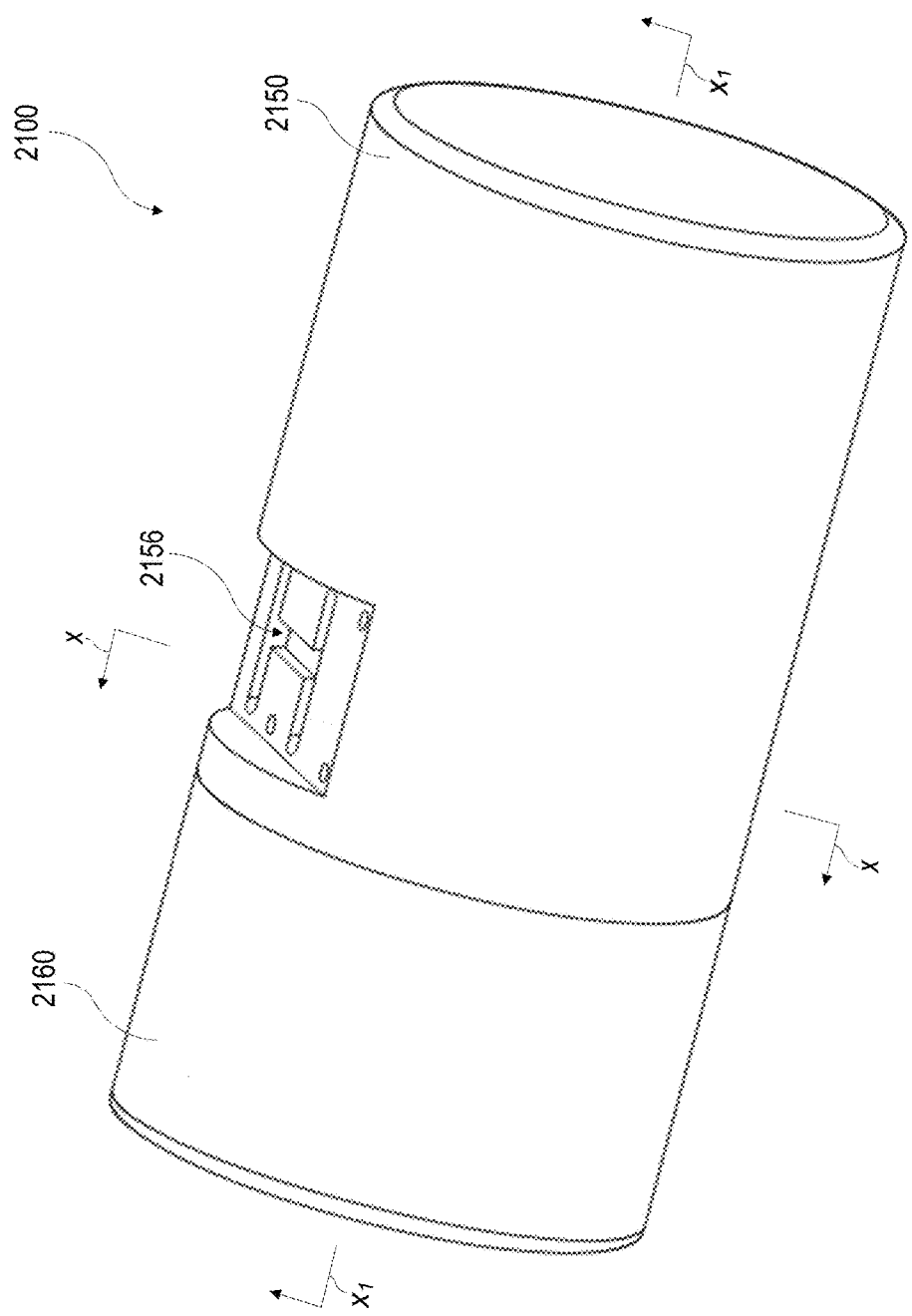
FIG. 5 is a perspective view of the sensor assembly of FIG. 3 with a gas-permeable filter removed for clarity.
Figure 8:
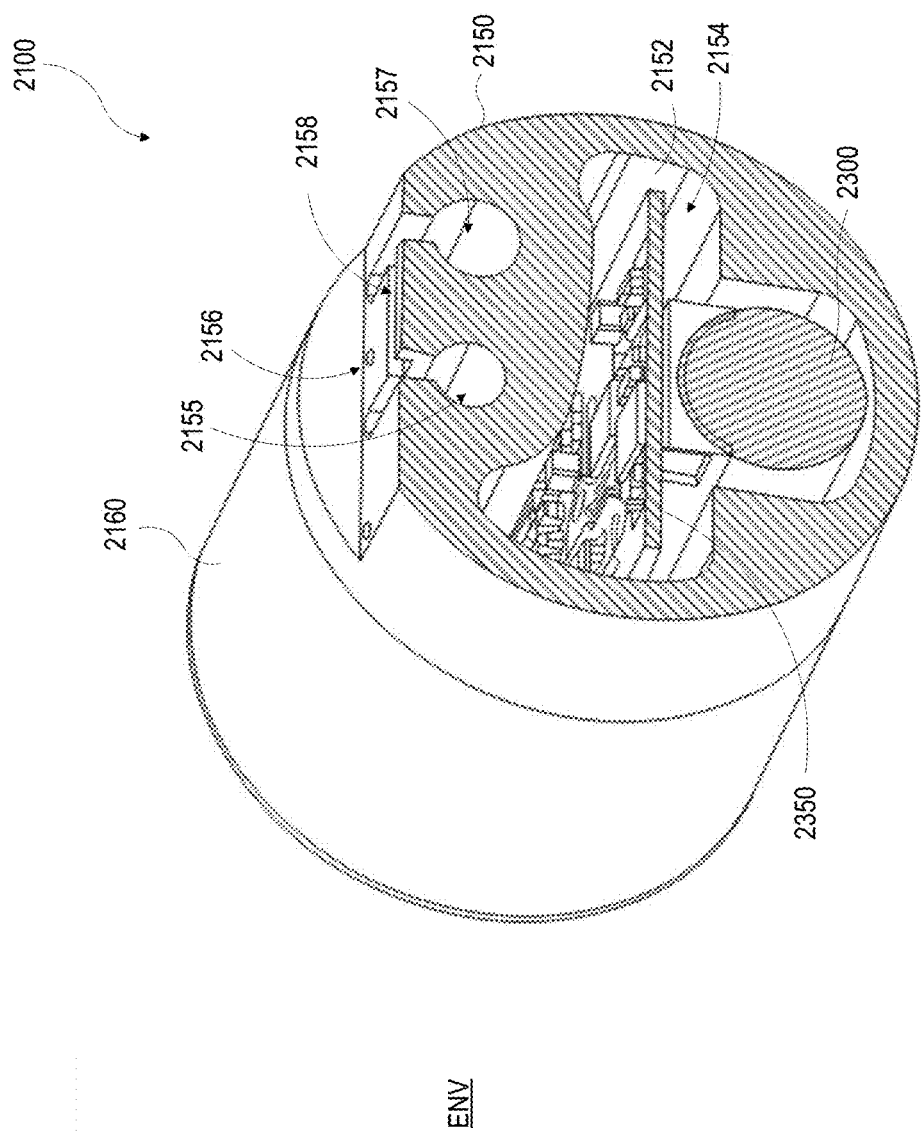
FIG. 8 is a cross-sectional view of the sensor assembly of FIG. 5 taken at line x-x.
Figure 9:
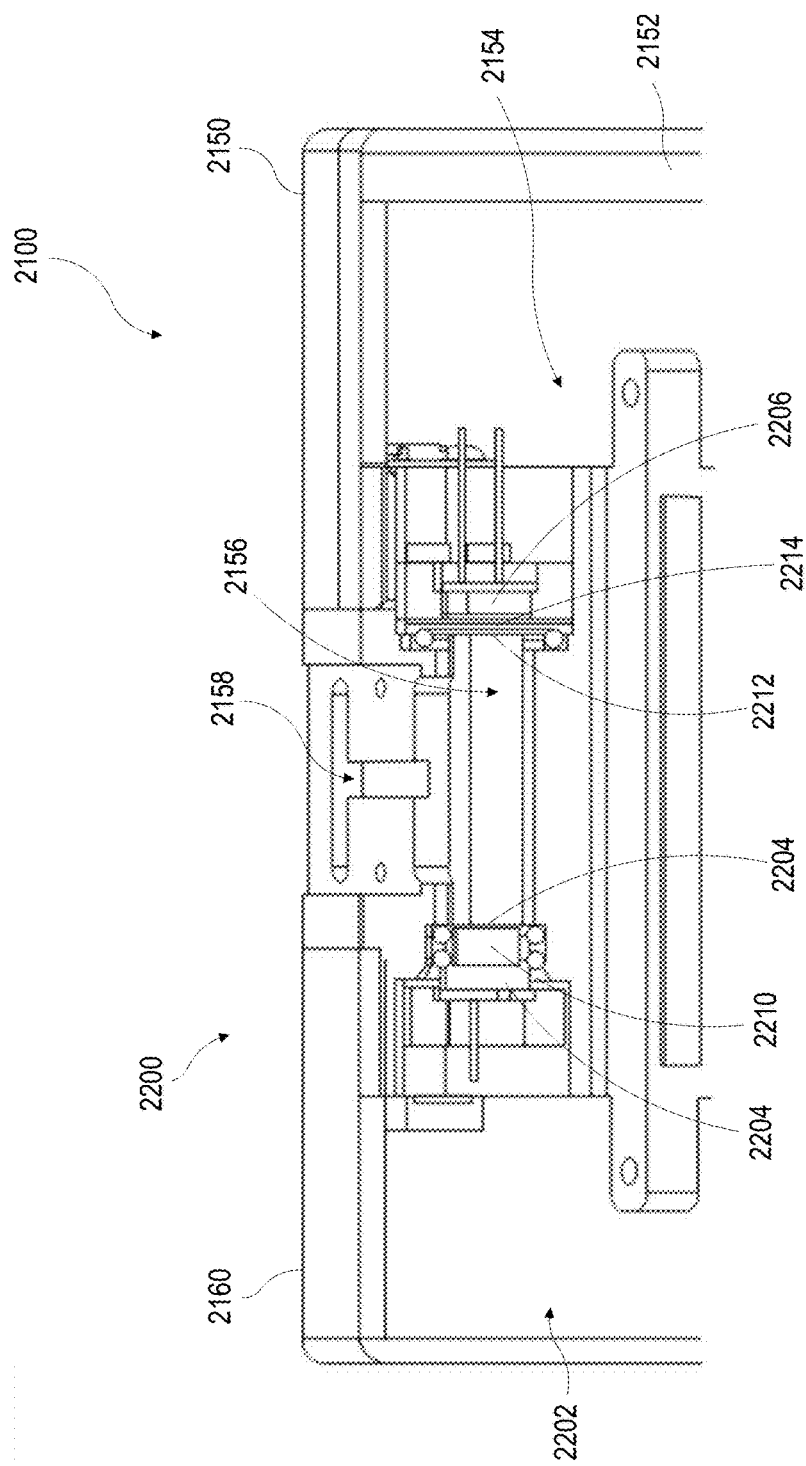
FIG. 9 is a cross-sectional view of a portion of the sensor assembly of FIG. 5 taken at line $x_1$-$x_1$.

FIG. 8 is a cross-sectional view of the sensor assembly of FIG. 5 taken at line x-x, while FIG. 9 is a cross-sectional view of a portion of the sensor assembly of FIG. 5 taken at line $x_1$-$x_1$. As depicted, the housing 2150 includes a wall 2152 that can, in some embodiments, be formed from a noncombustible and/or non-sparking material. For example, housing can be formed from aluminum or stainless steel. The wall 2152 defines an internal chamber 2154 and a sensing volume 2156. The sensing volume 2156 is in fluid communication with the sterilization environment ENV. The sensing volume 2156 is fluidically isolated from the internal chamber 2154. Additionally, the internal chamber 2154 can be fluidically isolated from the sterilization environment ENV. In some embodiments, the internal chamber 2154 can be hermetically sealed. Said another way, the internal chamber 2154 can be configured to be fully sealed such that an interaction between any electronics and/or polymer materials placed therein and the sterilization environment ENV is eliminated or minimized. This arrangement facilitates using the sensor assembly 2100 in such a flammable and/or explosive environment.

Figure 4:
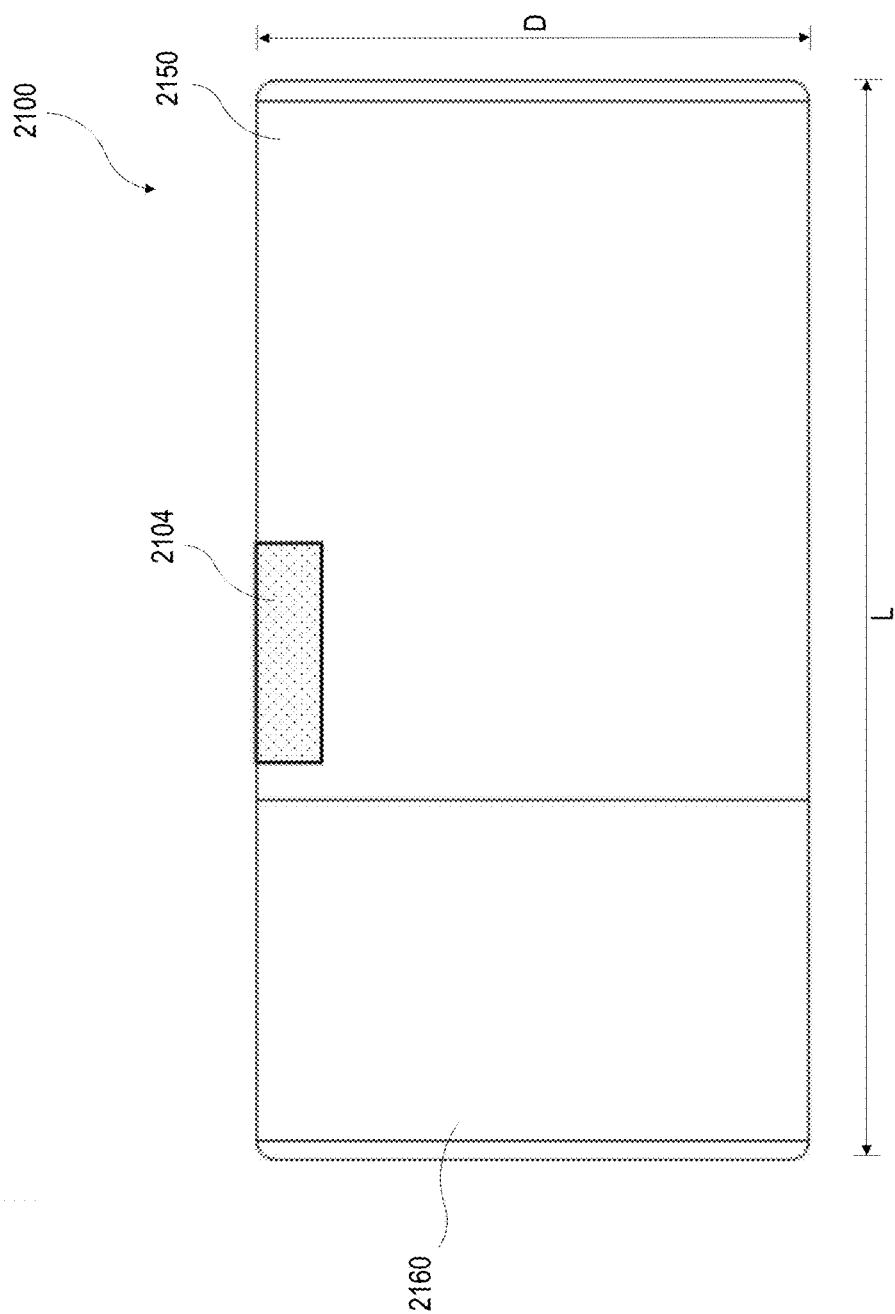
FIG. 4 is a side view of the sensor assembly of FIG. 3.

As depicted in FIGS. 3 and 4, in some embodiments, the fluid communication between the sensing volume 2156 and the sterilization environment ENV is via a gas-permeable filter 2104 that at least partially surrounds the housing 2150. The gas-permeable filter 2104 can preclude passage of particles or objects larger than the gas molecules within the sterilization environment ENV while permitting passage of the gas molecules from the sterilization environment ENV into the sensing volume 2156. The gas-permeable filter 2104 is omitted from FIGS. 5-9 for clarity.

Figure 6:
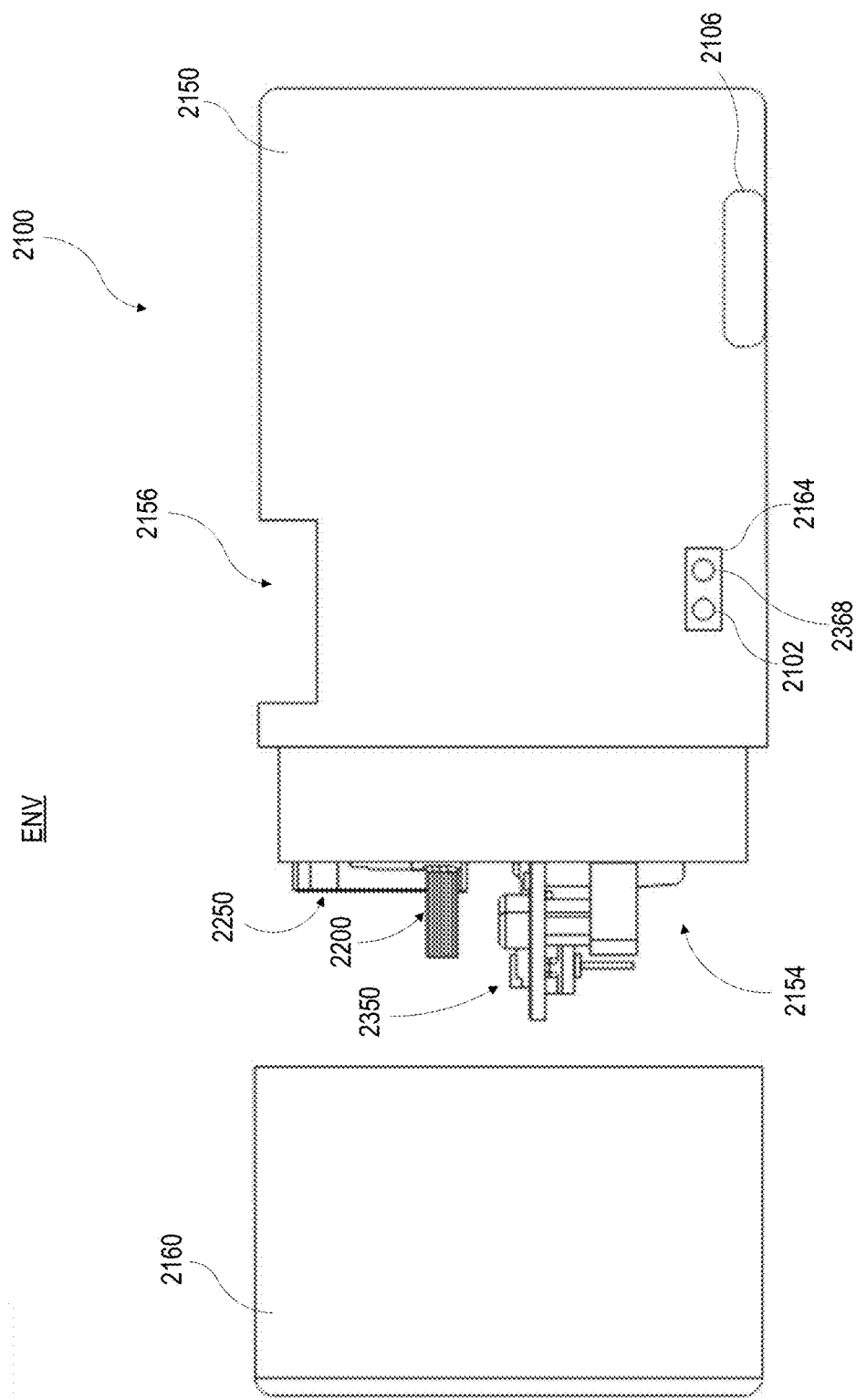
FIG. 6 is a side view of the sensor assembly of FIG. 5 with an end cap separated from a housing of the sensor assembly according to an embodiment.
Figure 7:
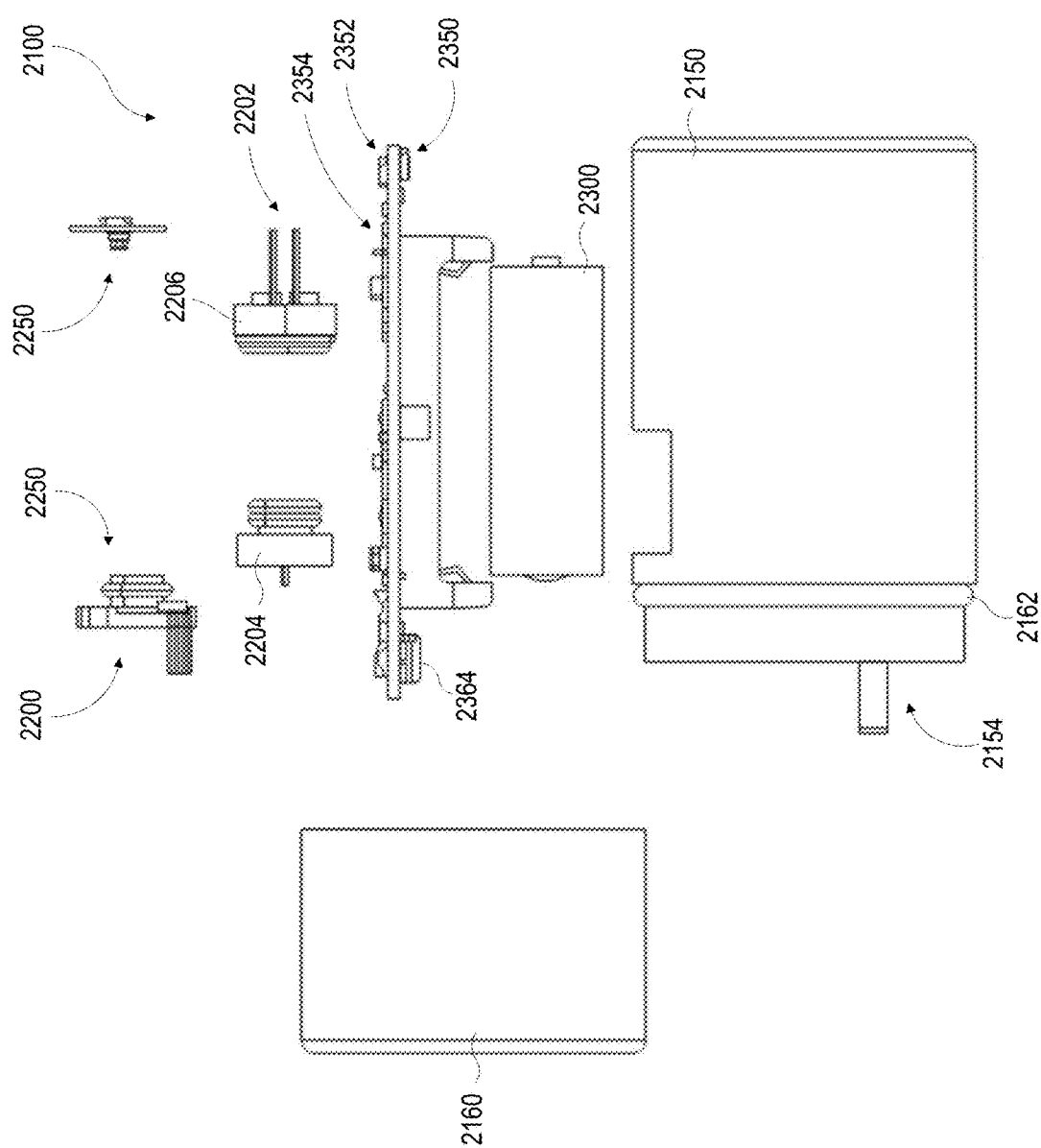
FIG. 7 is an exploded view of the sensor assembly of FIG. 5.

As depicted in FIGS. 6 and 7, in some embodiments, the sensor assembly 2100 includes an end cap 2160 (e.g., a cover) and a seal member 2162. The end cap 2160 can be removably coupled to the housing 2150 with the seal member 2162 being positioned between a portion of the end cap 2160 and the housing 2150. Accordingly, the coupling of the end cap 2160 and the seal member 2162 to the housing 2150 can hermetically seal the internal chamber 2154. Additionally, the removal of the end cap 2160 from the housing 2150 on a condition that the sensor assembly 2100 is outside of the sterilization chamber can facilitate access to components positioned within the internal chamber 2154.

As depicted in FIG. 6, in some embodiments, the sensor assembly 2100 can include a breach indicator 2102. The breach indicator 2102 is positioned within the internal chamber 2154. The breach indicator 2102 is configured to generate a signal should the hermetic seal of the internal chamber 2154 fail, resulting in the internal chamber 2154 (and the components contained therein) being exposed to the sterilant gas. In some embodiments, the signal can be a visual signal. In such embodiments, breach indicator 2102 can be visible via an observation portion 2164 (e.g., a visually transparent portion of the wall 2152) of the housing 2150. The breach indicator 2102 can, for example, be a chemical indicator that has a first color and a second color. The first color can be indicative of an absence of exposure to the sterilant gas, while the second color can be indicative of an exposure to the sterilant gas. The chemical indicator can be nonreactive to environmental conditions outside of the sterilization chamber. Accordingly, the internal chamber 2154 can be disrupted (e.g., open) on a condition that the sensor assembly 2100 is positioned outside of the sterilization chamber without causing the chemical indicator to transition from the first color to the second color.

As further depicted in FIG. 6, in some embodiments, the sensor assembly 2100 can include a positioning device 2106. The positioning device 2106 can be used to position the sensor assembly 2100 at a specified three-dimensional location within the sterilization chamber. The positioning device 2106 can, for example, be an actuatable magnet, a vacuum grip, a mechanical grip, an adhesive, a keyed protrusion, and/or a lanyard. Thus, the positioning device 2106 can be used to establish the sensor assembly 2100 at the specified three-dimensional location by securing the sensor assembly 2100 to a wall of the sterilization chamber, a support structure within the sterilization chamber, a product support, or a suspended sensor support on a condition that the sensor assembly is positioned within the sterilization chamber.

In some embodiments, the gas concentration sensor 2200 is positioned within the internal chamber 2154 and is operably coupled to the sensing volume 2156. Being operably coupled to the sensing volume 2156, which is in fluid communication with the sterilization environment ENV, the gas concentration sensor 2200 is positioned to monitor a concentration of the sterilant gas within the sterilization environment ENV. For example, in some embodiments, the sterilization environment ENV includes an invisible sterilant gas, such as ethylene oxide, and the gas concentration sensor 2200 can, as depicted in FIGS. 7 and 9, be a non-dispersive infrared gas concentration sensor 2202. The non-dispersive infrared gas concentration sensor 2202 can transmit and receive infrared radiation through the sensing volume 2156 via a window (e.g., a sapphire window) in order to determine the concentration of the invisible sterilant gas based on a detected decrease in transmitted infrared radiation within the sensing volume 2156.

As depicted in FIGS. 7 and 9, the gas concentration sensor 2200 configured as the non-dispersive infrared gas concentration sensor 2202 can include an emitter portion 2204 and a detector portion 2206 that are each operably coupled to the sensing volume 2156. At least a portion of the sensing volume 2156 is positioned between the emitter portion 2204 and the detector portion 2206. For example, in some embodiments, the emitter portion 2204 and the detector portion 2206 can be positioned on opposite sides of the sensing volume 2156.

In some embodiments, the emitter portion 2204 is an emitter of infrared radiation into (e.g., across) the sensing volume 2156. For example, the emitter portion 2204 can be blackbody emitter. In some embodiments, however, the emitter portion 2204 can be a light-emitting-diode emitter or laser diode emitter depending on the target wavelength of the emitted energy. The detector portion 2206 is positioned to receive a portion of the emitted infrared radiation from the emitter portion 2204 that is not absorbed by the sterilant gas within the sensing volume 2156. With the absorbed portion of the emitted infrared radiation being indicative of the concentration of the sterilant gas within the sensing volume 2156, the non-dispersive infrared gas concentration sensor 2202 is configured to output a signal corresponding to the concentration of the invisible sterilant gas within the sensing volume 2156 based on the difference between the magnitude of the emitted infrared radiation and the magnitude of the received infrared radiation.

The non-dispersive infrared gas concentration sensor 2202 can, in some embodiments, be at least a two-channel sensor having a measurement channel and a reference channel. The measurement channel can have a target wavelength associated with the known infrared absorbance signature of the invisible sterilant gas (e.g., the infrared absorbance signature of ethylene oxide). For example, the measurement channel can be filtered to target a wavelength associated with ethylene oxide (e.g., 3.2 µm). The reference channel can have a target wavelength associated with the absorbance of neither the sterilant gas nor an environmental gas. For example, the reference channel can be filtered to target a wavelength of 4 µm. In some embodiments the non-dispersive infrared gas concentration sensor 2202 can be a four-channel sensor. One of the additional channels can, for example, be used to measure water vapor, thereby reducing/eliminating the monitoring of humidity via an environmental sensor 2250. As an additional example, one of the additional channels can be filtered to have a target wavelength in the range of 6 µm to 7 µm in order to monitor other gases of interest within the sterilization environment ENV. At least one of the additional channels can also be filtered as an additional reference channel to improve the accuracy of the output signal.

As depicted in FIG. 9, in some embodiments, the non-dispersive infrared gas concentration sensor 2202 includes an emitter window 2208. The emitter window 2208 is positioned between the emitter portion 2204 and the sensing volume 2156. In other words, the emitter window 2208 can preclude physical contact between the emitter portion 2204 and the sterilant gas within the sensing volume 2156. The emitter window 2208 can, for example, be a sapphire window, a silicon window, or a window formed from another suitable composite. The emitter window 2208 can be substantially transparent in the wavelengths of the energy emitted (e.g., infrared energy) by the emitter portion 2204. In some embodiments, the emitter window 2208 has a low heat capacity and is at least partially absorptive of blackbody radiation (e.g., such as generated by the emitter portion 2204). In some embodiments, the emitter window 2208 is absorptive of blackbody radiation in a range outside of the detector channels ranges. For example, the emitter window 2208 can demonstrate absorbance in 5.5-20 microns wavelengths, but is not absorbent of wavelengths in a range of 3 microns to 4.5 microns, which can correspond to a detection wavelength range of the non-dispersive infrared gas concentration sensor 2202.

In embodiments wherein the emitter window 2208 is absorbative of blackbody radiation, the temperature of the emitter window 2208 can be increased by the passage of the energy radiated by the emitter portion 2204. Warming the emitter window 2208 can reduce or eliminate condensation that may otherwise develop on a surface of the emitter window 2208 due to differences in temperature and humidity between the sensing volume 2156 and the internal chamber 2154. A buildup of condensation on the emitter window 2208 can negatively affect the performance of the non-dispersive infrared gas concentration sensor 2202. For example, condensation resulting from variable swings in temperature, pressure, and humidity can result in abnormal reflections and dispersions that negatively affect the accuracy and sensitivity of the non-dispersive infrared gas concentration sensor 2202. Therefore, it is desirable to manage the temperature of the emitter window 2208 to eliminate or minimize condensation buildup.

In some embodiments, the non-dispersive infrared gas concentration sensor 2202 includes a window heater 2210 that is operably coupled to the emitter window 2208. The window heater 2210 is powered by the energy storage device 2300 and can be controlled by the sensor-assembly controller 2350. The window heater 2210 can, for example, include heating elements that are adhesively bonded to one face of the emitter window 2208. The heating elements can be resistive elements formed from metals, carbon, and/or other conductive elements. In some embodiments, the heating elements can be printed onto or etched into the face of the emitter window 2208 in a geometric pattern that optimizes heating efficiency without obstructing the passage of the infrared energy from the emitter portion 2204 into the sensing volume 2156. In some embodiments, the window heater 2210 can serve to augment the warming of the emitter window 2208 via the passage of the energy radiated by the emitter portion 2204 under specified conditions within the gas sterilization environment ENV.

In some embodiments, the non-dispersive infrared gas concentration sensor 2202 can include a receiver window 2212. The receiver window 2212 can be positioned between the detector portion 2206 and the emitter portion 2204 of the non-dispersive infrared gas concentration sensor 2202. Said another way, the receiver window 2212 can preclude physical contact between the detector portion 2206 and the sterilant gas within the sensing volume 2156. The receiver window 2212 can, for example, be a sapphire window, a silicon window, or a window formed from another suitable composite. The receiver window 2212 can be substantially transparent in the wavelengths of the energy emitted by the emitter portion 2204 such that the infrared emissions of the emitter portion 2204 are detectable by the detector portion 2206 after passing through the receiver window 2212. In some embodiments, the receiver window 2212 has a low heat capacity and is at least partially absorptive of blackbody radiation (e.g., such as generated by the emitter portion 2204). In some embodiments, the receiver window 2212 is absorptive of blackbody radiation in a range outside of the detector channels ranges. For example, the receiver window 2212 can demonstrate absorbance in 5.5-20 microns wavelengths, but is not absorbent of wavelengths in a range of 3 microns to 4.5 microns, which can correspond to a detection wavelength range of the non-dispersive infrared gas concentration sensor 2202.

In embodiments wherein the receiver window 2212 is absorbative of blackbody radiation, the temperature of the receiver window 2212 can be increased by the passage of the energy radiated by the emitter portion 2204. Warming the receiver window 2212 can reduce or eliminate condensation that may otherwise develop on a surface of the emitter window 2208 due to differences in temperature and humidity between the sensing volume 2156 and the internal chamber 2154. A buildup of condensation on the receiver window 2212 can negatively affect the detection of the non-absorbed portion of the infrared energy radiated by the emitter portion 2204. Said another way, condensation resulting from variable swings in temperature, pressure, and humidity can result in abnormal reflections and dispersions that negatively affect the accuracy and sensitivity of the non-dispersive infrared gas concentration sensor 2202. Therefore, it is desirable to manage the temperature of the receiver window 2212 to eliminate or minimize condensation buildup.

In some embodiments, the non-dispersive infrared gas concentration sensor 2202 includes a window heater 2214 that is operably coupled to the receiver window 2212. The window heater 2214 is powered by the energy storage device 2300 and can be controlled by the sensor-assembly controller 2350. The window heater 2214 can, for example, include heating elements that are adhesively bonded to one face of the receiver window 2212. The heating elements can be resistive elements formed from metals, carbon, and/or other conductive elements. In some embodiments, the heating elements can be printed onto or etched into the face of the receiver window 2212 in a geometric pattern that optimizes heating efficiency without obstructing the passage of the infrared energy from the sensing volume 2156 and onto the detector portion 2206. In some embodiments, the window heater 2214 can serve to augment the warming of the receiver window 2212 via the passage of the energy radiated by the emitter portion 2204 under specified conditions within the gas sterilization environment ENV.

In some embodiments, the window heater 2214 can be operably coupled to the receiver window 2212, while the emitter window 2208 has an absence of heating elements. In such embodiments, the temperature of the emitter window 2208 can, for example, be increased by the passage of the energy radiated by the emitter portion 2204, while the temperature of the receiver window 2212 is increased via the window heater 2214.

As depicted in FIGS. 6 and 7, in some embodiments, each environmental sensor 2250 is positioned within the internal chamber 2154. Each environmental sensor 2250 is also operably coupled to the sensing volume 2156. The operable coupling of each environmental sensor 2250 to the sensing volume 2156 can be via a sensor membrane or other sensor surface that is nonreactive with the sterilant gas. The environmental sensor 2250 can, for example, be a pressure sensor, a temperature sensor, and/or a humidity sensor. In some embodiments, the environmental sensor 2250 (i.e., a first environmental sensor) can be the pressure sensor and the sensor assembly 2100 can also include a separate, integrated sensor package (i.e., a second environmental sensor) that includes a combined humidity sensor and temperature sensor. The environmental sensor(s) 2250, can, therefore, be used to measure an ambient temperature, a humidity, and/or a pressure level of the sterilization environment ENV.

In some embodiments, the environmental sensor(s) 2250 (e.g., a humidity sensor) is self-heating. The self-heating can mitigate an effect of condensation on the environmental sensor(s) 2250 following an exposure to the sterilant gas. In some embodiments, the self-heating functionality of the environmental sensor(s) 2250 can be activated only on a condition that the sensor assembly 2100 is coupled to an external power source, such as following the sterilization period. In such embodiments, the self-heating functionality can restore/reset at least one function of the environmental sensor(s) 2250 following exposure to the extreme conditions of the sterilization environment ENV.

In some embodiments, gas concentration sensor 2200 and the environmental sensor(s) 2250 are operably coupled to different portions of the sensing volume 2156. For example, the gas concentration sensor 2200 can be operably coupled to a first portion 2155 of the sensing volume 2156, while the environmental sensor(s) 2250 is operably coupled to a second portion 2157 of the sensing volume 2156. As depicted in FIG. 8, The first portion 2155 and the second portion 2157 are fluidically coupled to the sterilization environment ENV via a communication passage 2158. A longitudinal axis of the first portion 2155 of the sensing volume 2156 is parallel to a longitudinal axis $A_{LO}$ (FIG. 3) of the housing 1150. Likewise, a longitudinal axis of the second portion 2157 of the sensing volume 2156 is parallel to a longitudinal axis $A_{LO}$ of the housing 1150. Accordingly, the longitudinal axis of the first portion 2155 is parallel to the longitudinal axis of the second portion 2157. Additionally, the first portion 2155 and the second portion 2157 are each positioned at a distance from an axial midline (e.g., the longitudinal axis $A_{LO}$) of the housing 2150 with the axial midline being between the first portion 2155 and the second portion 2157. This arrangement allows for a sufficient and consistent amount of the gas from the sterilization environment ENV to be conveyed into each of the first portion 2155 and the second portion 2157 for measurement.

With reference to FIGS. 7 and 8, the energy storage device 2300 is positioned within the internal chamber 2154. The energy storage device 2300 is operably coupled to the gas concentration sensor 2200, each environmental sensor 2250, the sensor-assembly controller 2350, and any additional electronic components of the sensor assembly 2100, such as window heaters 2210, 2214. Being positioned within the internal chamber 2154, the physical dimensions of the energy storage device 2300 are constrained to be less than the volume of the sensor assembly 2100 defined by the housing 2150. Accordingly, the capacity of the energy storage device 2300 is limited, at least in part, by the limited physical dimensions of the energy storage device 2300 necessary to position the energy storage device 2300 within the internal chamber 2154.

In some embodiments, the energy storage device 2300 can be a battery that has previously passed intrinsic safety testing. The energy storage device 2300 can be rechargeable or replaceable on a condition that the sensor assembly 2100 is positioned outside of the sterilization chamber. For example, a charging port can be positioned within the internal chamber 2154 and accessed by opening (e.g., unsealing) a portion of the housing 2150, such as the end cap 2160.

The energy storage device 2300 (e.g., the battery) can have a sufficient capacity to maintain operations of the powered components of the sensor assembly 2100 during the entirety of the sterilization period. The sterilization period is a continuous interval having a duration of at least six hours and no more than 48 hours. In some embodiments, the energy storage device 2300 can have a capacity in a range of 2.0 ampere-hours to 3.5 ampere-hours. For example, the battery can be a 3.0 ampere-hour battery with 8.7 watt-hours of total energy. In view of the absence of an external power source and capacity of the energy storage device 2300, in some embodiments, the sensor-assembly controller 2350, the gas concentration sensor 2200, the environmental sensor(s) 2250, and any additional powered components of the sensor assembly 2100 (e.g., such as window heaters 2210, 2214) have a combined maximal power draw in a range of between 50 mA and 275 mA (e.g., between 75 mA and 175 mA) and a combined average power draw during the sterilization period in a range of 0.15 watts and 0.35 watts. For example, the sensor-assembly controller 1350, the gas concentration sensor 1200, each environmental sensor 1250, and any additional powered components of the sensor assembly 1100 have a combined maximal current draw in a range of between 50 mA per hour and 275 mA per hour (e.g., between 75 mA per hour and 175 mA per hour). Said another way, being that the sensor assembly 2100 has an absence of an external power source, the capacity of the energy storage device 2300 defines the assets portion of the power budget for the sensor assembly 2100, while the maximal and average power draw of the electronic components of the sensor assembly 2100 for the duration of the sterilization period define the requirements portion of the power budget.

As depicted in FIGS. 6 and 8, in some embodiments, the sensor-assembly controller 2350 can be positioned within the internal chamber 2154. The sensor-assembly controller 2350 includes a processor 2352 and a memory module 2354 and is operably coupled to at least the gas concentration sensor 2200, each environmental sensor 2250, and the energy storage device 2300. The processor 2352 is configured to execute a series of stored instructions to control the operations of the sensor assembly 2100. The memory module 2354 can store the instructions for execution by the processor 2352. The memory module 2354 can also record output signals received from the gas concentration sensor 2200 and output signals received from the environmental sensor(s) 2250 at each sampling interval over a sterilization period of at least six hours and no more than 48 hours. The output signals received from the gas concentration sensor 2200 and the output signal received from the environmental sensor(s) 2250 are descriptive of the process state variables within the sterilization environment ENV at each sampling interval during the sterilization period. The process state variables recorded by the sensor-assembly controller 2350 are indicative of the gas sterilization process and can be used to verify that the process state variables satisfy the sterilization parameters. In other embodiments, the sterilization period can be between about six hours and 36 hours. In yet other embodiments, the sterilization period can be between about six hours and 24 hours.

As depicted in FIG. 7, in some embodiments, the sensor-assembly controller 2350 includes a data port 2364. The data port 2364 can be positioned within the internal chamber 2154. Being positioned within the internal chamber 2154, the data port 2364 is isolated from the sterilization environment ENV on a condition that the internal chamber 2154 is hermetically sealed. Accordingly, in some embodiments, access to the data port 2364 is available only on a condition that the end cap 2160 is decoupled from the housing 2150.

In some embodiments, the sensor-assembly controller 2350 can also be operably coupled to a wireless transmitter (not shown). The wireless transmitter can have an output signal that is configured to be received by an antenna element within the sterilization chamber during the sterilization period. In such embodiments, the wireless transmitter can be used to transmit the output signals received from the gas concentration sensor 2200 and/or the environmental sensor(s) 2250 to facilitate modifications to the process state variables during the sterilization period. For example, should the output from the gas concentration sensor 2200 indicate a concentration of ethylene oxide that exceeds a required minimum, the quantity of ethylene oxide introduced into the sterilization chamber can be reduced.

As depicted in FIG. 6, in some embodiments, the sensor assembly 2100 includes a status indicator 2368 that is operably coupled to the sensor-assembly controller 2350. The status indicator 2368 is configured to produce an indication of an operating status of the sensor assembly 2100. In some embodiments, a status indicator 2368 is positioned within the internal chamber 2154 and is visible through an observation portion 2164 of the housing 2150. The observation portion 2164 can be a visually transparent portion of the wall 2152.

In some embodiments, the sensor-assembly controller 2350 is configured to execute a set of operations to control the sensor assembly 2100 to monitor the sterilization environment ENV over the sterilization period. In some embodiments, the sensor-assembly controller 2350 is configured to perform the set of operations while disconnected at least from any external power source and any external instrument. In some embodiments, the set of operations can be performed while the sensor-assembly controller 2350 is also disconnected from an external memory device.

Figure 10:
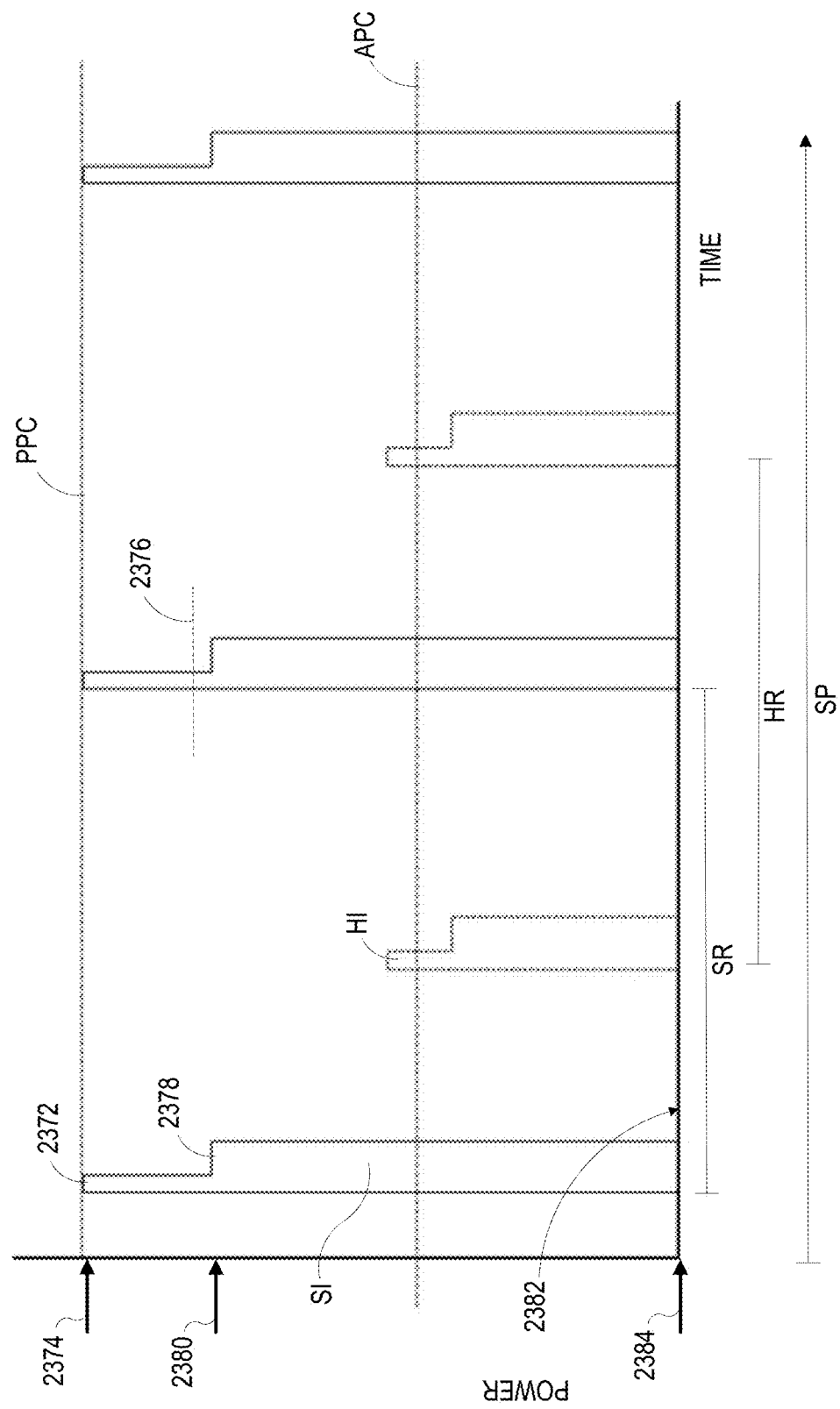
FIG. 10 is a graphical depiction of a sterilization period according to an embodiment.

With reference to FIG. 10, in some embodiments, the operations executed by the sensor-assembly controller 2350 manage a peak power consumption PPC of the sensor assembly 2100. The peak power consumption PPC is the maximal power consumed by any combination of the electronic components of the sensor assembly 2100 at a given instant. Additionally, in some embodiments, the operations executed by the sensor-assembly controller 2350 manage an average power consumption APC of the sensor assembly 2100 over the duration of the sterilization period. A limit for the peak power consumption PPC and a limit for the average power consumption APC are based on the capacity of the energy storage device 2300. Said another way, the sensor-assembly controller 2350 controls the operations of the electronic components of the sensor assembly 2100 such that neither an instantaneous peak power consumption PPC nor the average power consumption APC are at such a magnitude that the capacity of the energy storage device 2300 is exceeded prior to the completion of the sterilization period SP on a condition that the sterilization period SP has a duration of at least six hours and no more than 48 hours. In other embodiments, the sterilization period can be between about six hours and 36 hours. In yet other embodiments, the sterilization period can be between about six hours and 24 hours.

As depicted in FIG. 10, the operations executed by the sensor-assembly controller 2350 include initiating a set of sampling intervals SI at a sampling rate SR for the gas concentration sensor 2200 and the environmental sensor(s) 2250. Each sampling interval SI is a temporal portion of the sterilization period SP during which both the gas concentration sensor 2200 and the environmental sensor(s) 2250 are actuated to sample the sterilization environment ENV. The sampling rate SR corresponds to a period between the initiation of subsequent sampling intervals. Said another way, the sampling rate is the frequency at which the gas concentration sensor 2200 and the environmental sensor(s) 2250 are actuated during the sterilization period SP. In some embodiments, the sampling rate SR can be established in a range of five seconds to 30 seconds (e.g., seven seconds to 15 seconds). In other words, the operations executed by the sensor-assembly controller 2350 can include sampling the sterilization environment ENV via the gas concentration sensor 2200 and the environmental sensor 2250 at a sampling rate SR of at least twice per minute and no more than 12 times per minute over the sterilization period SP. For example, the operations executed by the sensor-assembly controller 2350 can include sampling the sterilization environment ENV via the gas concentration sensor 2200 and the environmental sensor 2250 at a sampling rate SR of eight sample intervals SI (e.g., measurements) per minute. In some embodiments, the measurements obtained during the sample intervals SI over each one minute of the sterilization period SP can be averaged together to generate at least one average measurement (e.g., 1, 2, or 4) over each one minute of the sterilization period. The average measurement(s) can be the value presented to a user following removal of the sensor assembly 2100 from the sterilization chamber.

The gas concentration sensor 2200 and/or the environmental sensor(s) 2250 can have a design (e.g., nominal) 50% duty cycle, which corresponds to repeatedly operating one second at maximal power followed by one second at no power. The 50% duty cycle corresponds to a sampling rate of two seconds and can maximize a signal-to-noise ratio in the absence of a power constraint. However, due to the absence of an external power supply, the capacity of the energy storage device 2300 within the limited volume of the sensor assembly 2100, and the sterilization period SP having a duration of at least six hours and no more than 48 hours, in some embodiments, the sensor-assembly controller 2350 operates the gas concentration sensor 2200 and the environmental sensor(s) 2250 at a lower duty cycle (i.e., a slower/lower frequency sampling rate). For example, sensor-assembly controller 2350 can reduce the duty cycle of the gas concentration sensor 2200 and/or the environmental sensor(s) 2250 to a minimum required to obtain relevant indications of the parameters within the sterilization environment ENV. The establishment of the sampling rate SR in the range of five seconds to 30 seconds (e.g., seven seconds to 15 seconds) reduces the power consumption of the gas concentration sensor 2200 and the environmental sensor(s) 2250 throughout the sterilization period SP while still providing an accurate indication of the parameters within the sterilization environment ENV. Said another way, operating the gas concentration sensor 2200 and the environmental sensor(s) 2250 no more frequently than once every five seconds (e.g., once every seven seconds) lowers the power consumption of the sensors at a cost of a greater signal-to-noise ratio. Said yet another way, slowing the sampling rate SR facilitates compliance with the power budget while maintaining effective monitoring of the sterilization environment ENV during the entirety of the sterilization period SP.

As depicted in FIG. 10, in some embodiments, sampling interval SI includes an initiation phase 2372. The initiation phase 2372 has an initiation power consumption 2374. The initiation power consumption 2374 can have a magnitude that is in a range of 120% to 140% of a design power consumption magnitude 2376. The design power consumption magnitude 2376 can correspond to a designed power consumption of the sensors during a sampling operation. A measurement phase 2378 follows each initiation phase 2372. The measurement phase 2378 has a measurement power consumption 2380 that is in a range of 80% to 100% of the design power consumption magnitude 2376 during an observation of the sterilization environment ENV.

Establishing the initiation power consumption 2374 at a magnitude that is greater than the design power consumption magnitude 2376 accelerates the time to a steady state signal during the measurement phase 2378. This, in turn, reduces the required duration of each sampling interval SI. Accordingly, measurement phase 2378 has a duration that is greater than a duration of the initiation phase 2372. For example, the initiation phase 2372 can have a duration that is in a range of 2% to 15% of the duration of the sampling interval SI. Due to the brevity of the initiation phase 2372 relative to the measurement phase 2378, the cost to the power budget of the greater initiation power consumption 2374 is outweighed by the benefit of the lower total power consumption during the sampling interval SI.

As further depicted in FIG. 10, each sampling interval SI is followed by a standby phase 2382. Said another way, the sensor-assembly controller 2350 initiates a standby phase 2382 following each measurement phase 2378 and preceding a subsequent initiation phase 2372. The standby phase 2382 has a standby power consumption 2384. The standby power consumption 2384 can be in a range of zero percent to 5% of the design power consumption magnitude 2376. In some embodiments, the standby phase 2382 has a duration that is greater than a combination of both the duration of the measurement phase 2378 and the duration of the initiation phase 2372. For example, in some embodiments, a ratio of the duration of the sampling interval SI to the standby phase 2382 can be in a range of 1:4 to 1:30. Increasing the duration of the standby phase 2382 results in a slower sampling rate SR, which corresponds to a decreased demand on the power budget in exchange for a decreased number of samples of the sterilization environment ENV.

In some embodiments, the operations executed by the sensor-assembly controller 2350 include activating the window heater 2210 and/or the window heater 2214 for a heating interval HI on a condition that the gas concentration sensor 2200 is in the standby phase 2382 as depicted in FIG. 10. Activating the window heater 2210 can, for example, include either transitioning the window heater 2210 from a non-powered state to a powered state or transitioning the window heater 2210 from a low-power state to a high-power state. In some embodiments, the window heater 2210 and/or the window heater 2214 can be actuated at a heating rate HR of between once per minute and 12 times per minute over the sterilization period SP. Limiting the initiation of the heating intervals HI to the standby phase 2382 of the sensors, precludes an undesirable increase in the peak power consumption PPC that would otherwise result if the initiation of a heating interval HI were to overlap with an initiation phase 2372. FIG. 10 depicts the heating intervals HI as being centered about the approximate midpoint of the sampling rate SR for clarity. However, in some embodiments, each heating interval HI can be initiated to immediately proceed the initiation of a sampling interval SI. Concluding each heating interval HI just prior to (e.g., concurrent with) the initiation of the following sampling interval SI can facilitate ensuring that the emitter window 2208 and/or the receiver window 2212 is not affected or minimally affected by condensation at the initiation of the sampling interval SI thereby improving the gas concentration sampling. Additionally, concluding each heating interval HI just prior to (e.g., concurrent with) the initiation of the following sampling interval SI can minimize or eliminate the signal interference that may otherwise result from background blackbody irradiation produced by the window heater 2214. In some embodiments, for example, the window heater 2214 can be activated between 0.5 seconds and 1.0 seconds following the conclusion of each heating interval HI and deactivated between 1.0 seconds and 0.5 seconds prior to the initiation of the following sampling interval SI.

Rather than actuating the window heater 2210 and/or the window heater 2214 in accordance with a heating rate HR, in some embodiments, the window heater 2210 and/or the window heater 2214 can be actuated based on the environmental conditions within the sterilization chamber. For example, the operations executed by the sensor-assembly controller 2350 can include determining, via the environmental sensor(s) 2250, an ambient temperature of the sterilization environment ENV. The window heater 2210 and/or the window heater 2214 can then be activated on a condition that the ambient temperature is below a minimum temperature threshold. The minimum temperature threshold corresponding to a temperature below which condensation formation on the emitter window 2208 and/or the receiver window 2212 may be expected. Similarly, the operations executed by the sensor-assembly controller 2350 can include determining a humidity level within the sterilization environment ENV. The window heater 2210 and/or the window heater 2214 can then be activated on a condition that the humidity level exceeds a humidity threshold. The humidity threshold corresponding to a humidity level of which condensation formation on the emitter window 2208 and/or the receiver window 2212 may be expected. In some embodiments, the actuation based on environment conditions can be delayed by the sensor-assembly controller 2350 when such actuation would correspond to the initiation of a sampling interval SI to preclude negatively affecting the peak power consumption PPC and/or the average power consumption and, therefore, the power budget.

In some embodiments, the window heater 2210 and/or the window heater 2214 can be activated in accordance with a first heating rate (e.g., a first heater duty cycle) on a condition that an ambient temperature is within a first temperature range. Similarly, the window heater 2210 and/or the window heater 2214 can be activated in accordance with second heating rate (e.g., a second heater duty cycle) on a condition that the ambient temperature is within a second temperature range. The second heating rate can have a duration between sequential heater actuations that is greater than a duration between sequential heater actuations of the first heating rate. In other words, when justified by the environmental conditions within the sterilization environment ENV, the window heater 2210 and/or the window heater 2214 can be activated more frequently than would otherwise be desirable to ensure accurate sampling of the sterilization parameters at a cost to the power budget.

In some embodiments, the sensor-assembly controller 2350 can apply a correction factor to the output of the gas concentration sensor 2200 based on the environmental conditions (e.g., the temperature and/or humidity) within the sterilization environment ENV. Accordingly, the sensor-assembly controller 2350 can, for example, determine an ambient temperature and/or humidity of the sterilization environment ENV at each sampling interval SI based on an output of the environmental sensor(s) 2250. The sensor-assembly controller 2350 can then determine a correction factor at each sampling interval SI for the output from the gas concentration sensor 2200 based on the ambient temperature and/or the humidity of the sterilization environment ENV at the sampling interval SI. The correction factor can then be applied to the output of the gas concentration sensor 2200 at each sampling interval SI to determine a recorded sterilant gas concentration (e.g., a concentration of ethylene oxide within the sensing volume 2156) at each sampling interval.

Figure 11:
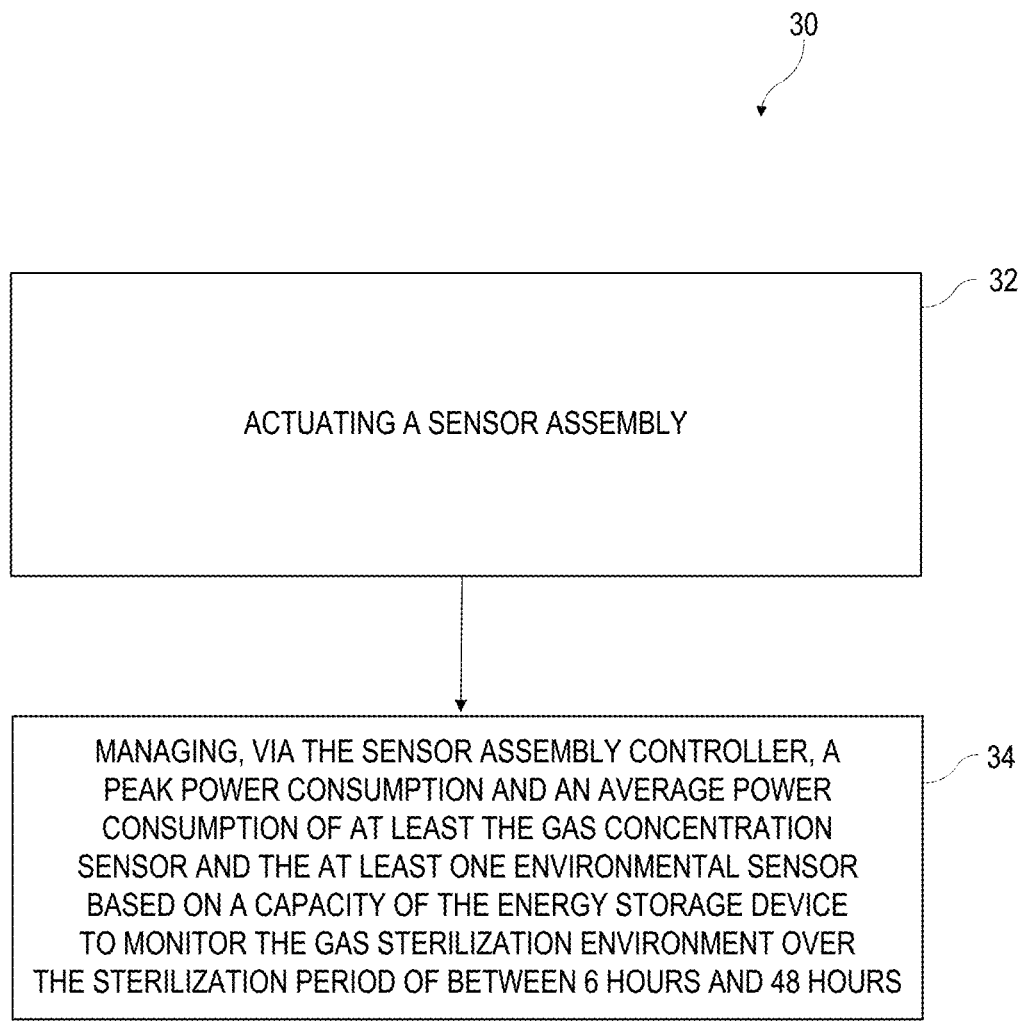
FIG. 11 is a flow chart of a method for monitoring a gas sterilization environment according to an embodiment.

FIG. 11 is a flow chart of a method 30 for monitoring a gas sterilization environment according to an embodiment. The method 30 can, in an embodiment, be performed via any of the sensor assemblies described herein, such as sensor assembly 1100 and sensor assembly 2100 with reference to FIGS. 1-10. However, it should be appreciated that in various embodiments, aspects of the method 30 can be accomplished via additional embodiments of the sensor assembly or components thereof. Accordingly, the method 30 can be implemented via any suitable sensor assembly. The method 30 can be implemented as a set of operations executed by a controller, such as the sensor-assembly controller 1350 and the sensor-assembly controller 2350 as described herein.

As depicted at 32, the method 30 includes actuating a sensor assembly positioned within a sterilization chamber. The sensor assembly includes a gas concentration sensor, at least one environmental sensor, an energy storage device, and a sensor-assembly controller configured to record a set of signals from the gas concentration sensor and the at least one environmental sensor associated with the sterilization environment at each sampling interval of a set of sampling intervals over a sterilization period of between six hours and 48 hours. The sensor assembly is devoid of any external data connections and power connections within the sterilization environment. As depicted at 34, the method 30 also includes managing, via the sensor-assembly controller, a peak power consumption and an average power consumption of at least the gas concentration sensor and the at least one environmental sensor based on a capacity of the energy storage device to monitor the gas sterilization environment over the sterilization period of between six hours and 48 hours.

In some embodiments, actuating the sensor assembly includes actuating the gas concentration sensor and the environmental sensor(s) at a sampling rate of at least twice per minute and no more than 12 times per minute over the sterilization period. For example, the method 30 can include actuating the gas concentration sensor and the environmental sensor(s) at a sampling rate of at least four times per minute and less than nine times per minute over the sterilization period. The method 30 can also include transitioning the gas concentration sensor and the environmental sensor(s) to an inactive state at a conclusion of each sampling interval of the set of sampling intervals.

As described herein, in some embodiments, each sampling interval of the set of sampling intervals includes an initiation phase followed by a measurement phase. The initiation phase can have a duration that is in a range of 2% to 15% of a duration of each sampling interval of the set of sampling intervals. In order to manage the peak power consumption during the sampling intervals, the method 30 can include establishing at least the gas concentration sensor at an initiation power consumption during the initiation phase. Additionally, to manage the average power consumption during the sterilization period, the method 30 can include transitioning at least the gas concentration sensor toward a measurement power consumption concurrent with a transition from the initiation phase to the measurement phase. The initiation power consumption can have a magnitude that is configured to minimize a time to a steady-state signal of at least the gas concentration sensor following an initiation of each sampling interval of the set of sampling intervals. The magnitude of the initiation power consumption can, for example, be in a range of at least 1.2 to no more than 1.4 times a magnitude of the measurement power consumption, while the measurement power consumption can be in a range of at least 0.8 to no more than 1.0 times a design power consumption magnitude of the gas concentration sensor and/or the environmental sensor(s).

In some embodiments, the method 30 can include activating at least one window heater operably coupled to a window positioned between the gas concentration sensor and a sensing volume. In some embodiments, the activation occurs on a condition in which at least a humidity level exceeds a humidity threshold and/or an ambient temperature is below a minimum temperature threshold. The window heater(s) is maintained in an inactive state on a condition in which both the humidity level is below the humidity threshold and the ambient temperature is above the minimum temperature threshold. In some embodiments, the window heater(s) can be activated only on a condition in which each of the gas concentration sensor and the environmental sensor(s) are in an inactive state. Accordingly, the window heater(s) is maintained in an inactive state during each sampling interval.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or microinstructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

The processor included within the sensor assembly (and any of the processors and/or controllers described herein) can be any processor configured to, for example, write data into and read data from the memory of the controller, and execute the instructions and/or methods stored within the memory. Furthermore, the processor can be configured to control operation of the other modules within the controller (e.g., the temperature feedback module and the flow module). Specifically, the processor can receive a signal including temperature data, current measurements or the like and determine an amount of power and/or current to be supplied to each heater assembly, the desired timing and sequence of the piston pulses and the like. For example, in some embodiments, the controller can be an 8-bit PIC microcontroller, which will control the power delivered to various components within the sensor assemblies described herein. This microcontroller can also contain code for and/or be configured to minimize the instantaneous power requirements on the power source.

In other embodiments, any of the processors described herein can be, for example, an application-specific integrated circuit (ASIC) or a combination of ASICs, which are designed to perform one or more specific functions. In yet other embodiments, the microprocessor can be an analog or digital circuit, or a combination of multiple circuits.

Any of the memory devices described herein can be any suitable device such as, for example, a read only memory (ROM) component, a random access memory (RAM) component, electronically programmable read only memory (EPROM), erasable electronically programmable read only memory (EEPROM), registers, cache memory, and/or flash memory. Any of the modules (the pressure feedback module and the position feedback module) can be implemented by the processor and/or stored within the memory.

Although various embodiments have been described as having particular features and/or combinations of components, other embodiments are possible having a combination of any features and/or components from any of embodiments as discussed above.

What is claimed is:

1. A sensor assembly for monitoring a gas sterilization environment, the sensor assembly comprising:
   a housing having a wall, the wall at least partially defining an internal chamber and a sensing volume, the sensing volume being in fluid communication with the gas sterilization environment and fluidically isolated from the internal chamber;
   a gas concentration sensor positioned within the internal chamber, the gas concentration sensor being operably coupled to the sensing volume;
   at least one environmental sensor positioned within the internal chamber, the at least one environmental sensor being operably coupled to the sensing volume;
   an energy storage device positioned within the internal chamber and operably coupled to the gas concentration sensor and the at least one environmental sensor; and
   a sensor-assembly controller including a processor and a memory module, the sensor-assembly controller being operably coupled to the gas concentration sensor, the at least one environmental sensor, and the energy storage device, the sensor-assembly controller being configured to execute a plurality of operations to monitor the gas sterilization environment over a sterilization period of between six hours and 48 hours.

2. The sensor assembly of claim 1, wherein:
the sensor assembly has a volume of between 150 milliliters and 450 milliliters defined by a plurality of maximal external dimensions of the sensor assembly.

3. The sensor assembly of claim 1, wherein:
the plurality of operations includes sampling via the gas concentration sensor and the at least one environmental sensor at a sampling rate of at least twice per minute and no more than 12 times per minute over the sterilization period; and
the sensor-assembly controller is configured to perform the plurality of operations while disconnected from any external power source and any external instrument.

4. The sensor assembly of claim 1, wherein:
the energy storage device has a capacity in a range of 2.0 ampere-hours to 3.5 ampere-hours.

5. The sensor assembly of claim 4, wherein:
the sensor-assembly controller, the gas concentration sensor, and the at least one environmental sensor have a combined maximal power draw in a range of 75 milliamperes and 175 milliamperes.

6. The sensor assembly of claim 4, wherein:
the sensor-assembly controller, the gas concentration sensor, and the at least one environmental sensor have a combined average power draw during the sterilization period in a range of 0.15 watts and 0.35 watts.

7. The sensor assembly of claim 1, further comprising:
an end cap and a seal member removably coupled to the housing, the end cap and the seal member hermetically sealing the internal chamber on a condition that the end cap and seal member are coupled to the housing.

8. The sensor assembly of claim 1, wherein:
the gas sterilization environment includes an invisible sterilant gas;
the gas concentration sensor is a non-dispersive infrared gas concentration sensor with an emitter portion and a detector portion;
the emitter portion and the detector portion are operably coupled to the sensing volume;
the non-dispersive infrared gas concentration sensor is configured to output a signal corresponding to a concentration of the invisible sterilant gas within the sensing volume,
the non-dispersive infrared gas concentration sensor includes a receiver window positioned between the detector portion and the emitter portion; and
the receiver window has a low heat capacity and is absorptive of blackbody radiation.

9. The sensor assembly of claim 8, wherein:
the non-dispersive infrared gas concentration sensor includes a window heater operably coupled to the receiver window;
the window heater is selectively actuated by the sensor-assembly controller; and
the plurality of operations includes actuating the window heater at a heating rate of at least twice per minute and no more than 12 times per minute over the sterilization period.

10. The sensor assembly of claim 1, wherein:
the plurality of operations executed by the sensor-assembly controller manage a peak power consumption and an average power consumption of at least the gas concentration sensor and the at least one environmental sensor based on a capacity of the energy storage device to monitor the gas sterilization environment over the sterilization period of between six hours and 48 hours.

11. The sensor assembly of claim 10, wherein:

the plurality of operations includes initiating a plurality of sampling intervals at a sampling rate for the gas concentration sensor and the at least one environmental sensor;

each sampling interval of the plurality of sampling intervals corresponds to a sampling of the gas sterilization environment via the gas concentration sensor and the at least one environmental sensor;

the sampling rate corresponds to a period between an initiation of subsequent sampling intervals; and the sampling rate is in a range of 5 seconds to 30 seconds during the sterilization period.

12. The sensor assembly of claim 11, wherein:

each sampling interval includes an initiation phase and a measurement phase following the initiation phase;

the initiation phase includes an initiation power consumption that is in a range 120 percent to 140 percent of a design power consumption magnitude;

the measurement phase includes a measurement power consumption that is in a range of 80 percent to 100 percent of the design power consumption magnitude during an observation of the gas sterilization environment;

the plurality of operations includes initiating a standby phase following the measurement phase and preceding a subsequent initiation phase; and the standby phase includes a standby power consumption in a range of 0 percent to 5 percent of the design power consumption magnitude.

13. A method for monitoring a gas sterilization environment, the method comprising:

actuating a sensor assembly, the sensor assembly including a gas concentration sensor, at least one environmental sensor, an energy storage device, and a sensor-assembly controller configured to record a plurality of signals from the gas concentration sensor and the at least one environmental sensor associated with the gas sterilization environment at each sampling interval of a plurality of sampling intervals over a sterilization period of between six hours and 48 hours, the sensor assembly being devoid of any external data connections and power connections within the gas sterilization environment; and managing, via the sensor-assembly controller, a peak power consumption and an average power consumption of at least the gas concentration sensor and the at least one environmental sensor based on a capacity of the energy storage device to monitor the gas sterilization environment over the sterilization period of between six hours and 48 hours.

14. The method of claim 13, further comprising:

transitioning the gas concentration sensor and the at least one environmental sensor to an inactive state at a conclusion of each sampling interval of the plurality of sampling intervals.

15. The method of claim 13, wherein:

each sampling interval of the plurality of sampling intervals includes an initiation phase followed by a measurement phase;

the initiation phase has a duration that is in a range of 2% to 15% of a duration of each sampling interval of the plurality of sampling intervals;

managing the peak power consumption includes establishing at least the gas concentration sensor at an initiation power consumption during the initiation phase;

managing the average power consumption includes transitioning at least the gas concentration sensor toward a measurement power consumption concurrent with a transition from the initiation phase to the measurement phase;

the initiation power consumption has a magnitude that is configured to minimize a time to a steady-state signal of at least the gas concentration sensor following an initiation of each sampling interval of the plurality of sampling intervals;

the magnitude of the initiation power consumption is in a range of at least 1.2 to no more than 1.4 times a magnitude of the measurement power consumption; and the measurement power consumption is in a range of at least 0.8 to no more than 1.0 times a design power consumption magnitude of the gas concentration sensor.

16. The method of claim 13, further comprising:

activating at least one window heater operably coupled to a window positioned between the gas concentration sensor and a sensing volume on a condition that each of the gas concentration sensor and the at least one environmental sensor are in an inactive state and maintaining the at least one window heater in an inactive state during each sampling interval of the plurality of sampling intervals.

17. The method of claim 13, wherein:

the gas concentration sensor includes at least one window positioned between a portion of the gas concentration sensor and a sensing volume;

the at least one window is absorptive of blackbody radiation emitted by the gas concentration sensor; and actuating the sensor assembly includes actuating the gas concentration sensor at a sampling rate configured to maintain the at least one window at a temperature within a specified temperature range.

18. A sensor assembly for monitoring a gas sterilization environment, the sensor assembly comprising:

a housing having a wall, the wall at least partially defining an internal chamber and a sensing volume, the sensing volume being in fluid communication with the gas sterilization environment and fluidically isolated from the internal chamber;

a cover removably coupled to the housing, the internal chamber being exposed on a condition that the cover is removed from the housing, the cover and a seal member hermetically sealing the internal chamber on a condition that the cover and seal member are coupled to the housing;

a gas concentration sensor positioned within the internal chamber, the gas concentration sensor being operably coupled to the sensing volume;

at least one environmental sensor positioned within the internal chamber, the at least one environmental sensor being operably coupled to the sensing volume;

an energy storage device positioned within the internal chamber and operably coupled to the gas concentration sensor and the at least one environmental sensor; and a sensor-assembly controller including a processor and a memory module, the sensor-assembly controller being operably coupled to the gas concentration sensor, the at least one environmental sensor, and the energy storage device, the sensor-assembly controller being configured to execute a plurality of operations to monitor the gas sterilization environment over a sterilization period.

19. The sensor assembly of claim 18, wherein:
the sensor-assembly controller is configured to perform the plurality of operations while disconnected from any external power source and any external instrument.

20. The sensor assembly of claim 19, further comprising:
a breach indicator positioned within the internal chamber, the breach indicator being configured to generate a signal on a condition of a failure of a hermetic seal of the internal chamber.

\* \* \* \* \*